United States Patent [19]
Grover et al.

[11] Patent Number: 6,083,372
[45] Date of Patent: Jul. 4, 2000

[54] REAGENTS AND METHODS FOR PERFORMING ELECTROKINETIC CHROMATOGRAPHY

[75] Inventors: Edward R. Grover, Randolph; Michael E. Swartz, Uxbridge; Jeffrey R. Mazzeo, Chelmsford, all of Mass.

[73] Assignee: Waters Investments Limited, New Castle, Del.

[21] Appl. No.: 08/806,300

[22] Filed: Feb. 26, 1997

Related U.S. Application Data

[63] Continuation-in-part of application No. 08/503,462, Jul. 18, 1995, abandoned, and a continuation-in-part of application No. 08/585,049, Jan. 11, 1996, abandoned.

[51] Int. Cl.[7] .................................................. G01N 27/26
[52] U.S. Cl. ........................................ 204/451; 204/601
[58] Field of Search .................................. 204/451, 452, 204/453, 454, 601, 605

[56] References Cited

U.S. PATENT DOCUMENTS

| | | |
|---|---|---|
| 4,936,963 | 6/1990 | Mandecki et al. . |
| 5,084,150 | 1/1992 | Karger et al. ........................ 204/180.1 |
| 5,373,048 | 12/1994 | Witzeman et al. . |
| 5,445,947 | 8/1995 | Metz et al. . |
| 5,464,517 | 11/1995 | Hjerten et al. . |
| 5,482,866 | 1/1996 | Denton et al. . |

FOREIGN PATENT DOCUMENTS

| | | |
|---|---|---|
| 0 292 837 | 11/1988 | European Pat. Off. . |
| WO 93/05389 | 3/1993 | WIPO . |

OTHER PUBLICATIONS

Harakuwe, A., et al, Optimization of selectivity in capillary zone electrophoresis of inorganic anions using binary cationic surfactant mixtures. J.of Chromatoghr. A vol.:685 Issue 1 (abstract), Nov. 1994.

Mazzeo,J., et al, Novel chiral surfactant for the separation of enantiomers by micellar electrokinetic capillary chromatography. J. of Chromatoghr. A vol.:680, p. 125, Sep. 1994.

T. Schmitt/H. Engelhardt, Charged and Uncharged Cyclodextrins as Chiral Selectors in Capillary Electrophoresis, Chromatographia vol. 37, No. 9/Nov. 10, 1993.

D. Kaniansky, Role of The Charge Number of The Counter–Ionic Constituent in The Separation of Anions by Isotachophoresis, Journal of Chromatography 194 (1980) 11–19.

R. Kuhn, F. Stoecklin, Chiral Separations by Host–Guest Complexaation with Cyclodextrin and Crown Ether in Capillary Zone Electrophoresis Chromatographia vol. 33, No. 1/2 Jan. 1992.

David C. Tikle, et al., Glucopyranoside–Based Surfactants as Pseudostationary Phases for Chiral Separations in Capillary Electrophoresis, Analytical Chemistry 66(1994) Dec. 1, No. 23, Washington, DC.

Electrokinetic Chromatography with Micellar Solution and Open–Tubular Capillary Anal. Chem 1985, 57, 834–841, Shigeru Terabe, et al.

*Primary Examiner*—Robert J. Warden, Sr.
*Assistant Examiner*—Jennifer C. McNeil
*Attorney, Agent, or Firm*—Anthony J. Janiuk

[57] ABSTRACT

The invention is in the field of electrokinetic chromatography. In particular, the invention is directed to reagents and methods of performing electrokinetic chromatography. The reagents and methods afford fast, high resolution separations with increased detectability.

21 Claims, 23 Drawing Sheets

(S)-N-DODECOXYCARBONYLVALINE (S)-N-DODECOXYCARBONYLVALINE

BIS-TRIS PROPANE

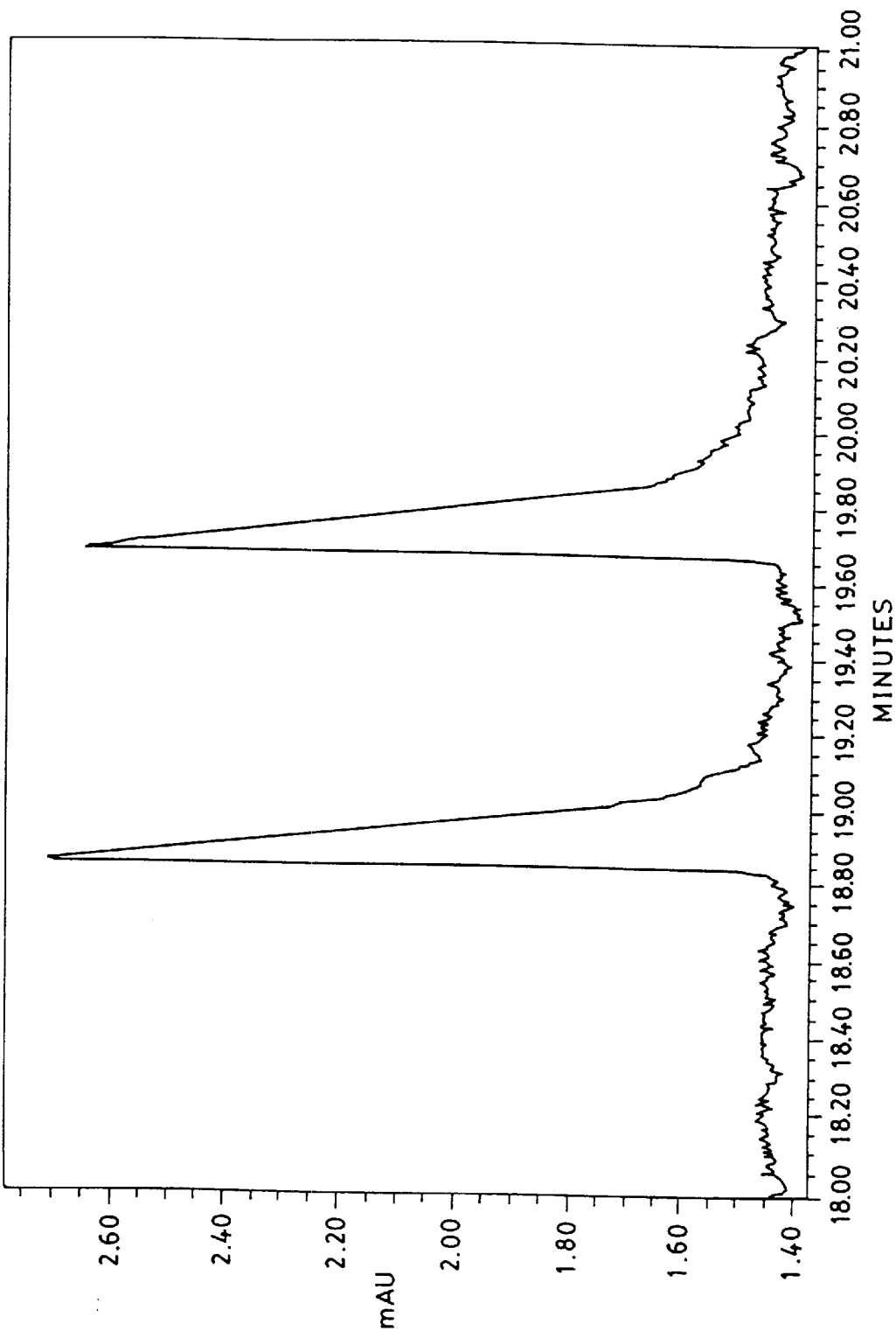

$NH_2CH_2CH_2NHCH_2CH_2CH_2NHCH_2CH_2NH_2$

N,N'-bis-(2-aminoethyl)-1,13-propanediamine $CH_3CH(OH)CH_2N\{CH_2CH_2CH_2N[CH_2CH(OH)CH_3]_2\}_2$ pentrol $NH_2CH_2CH_2NHCH_2CH_2CH_2NHCH_2CH_2NHCH_2CH_2NHCH_2CH_2NH_2$ pentaethylenehexamine $O[CH_2CH_2O(CH_2)_3NH_2]_2$ 4,7,10-trioxa-1,13-tridecanediamine

FIG. 8

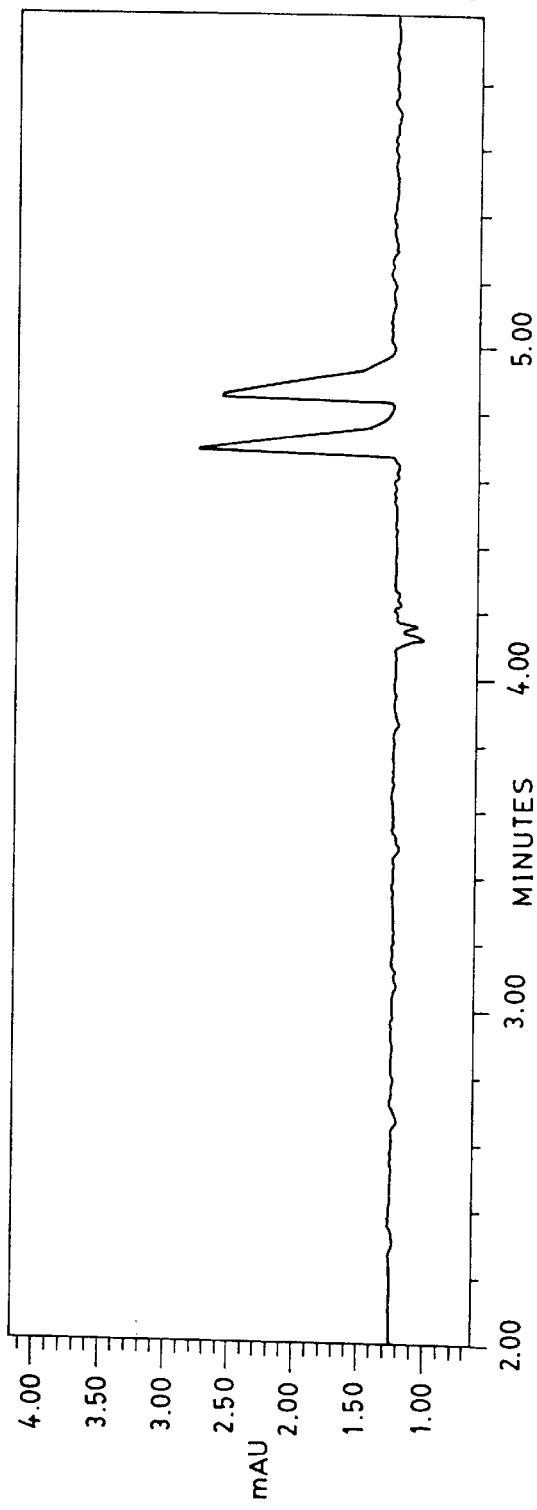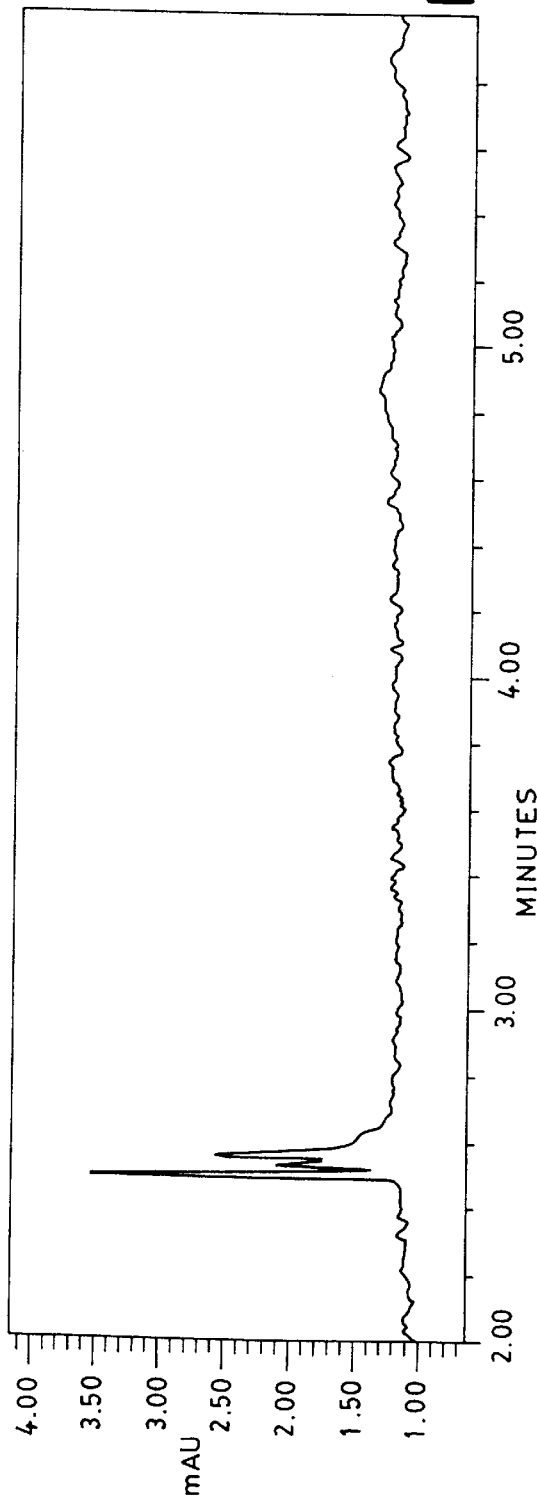

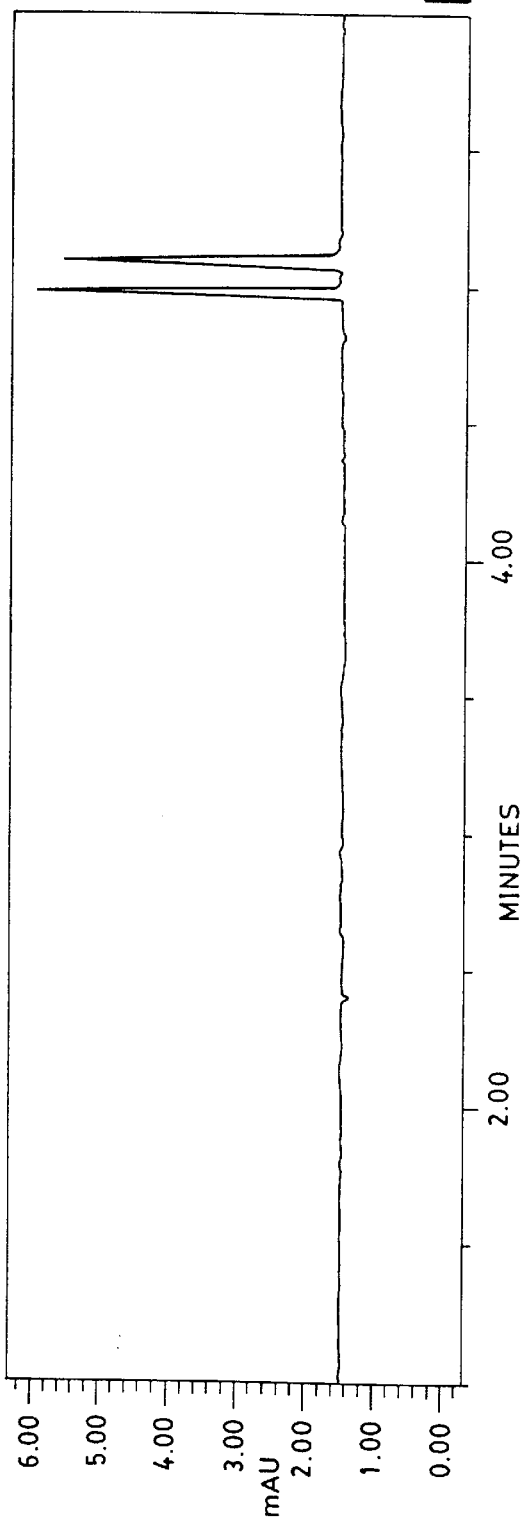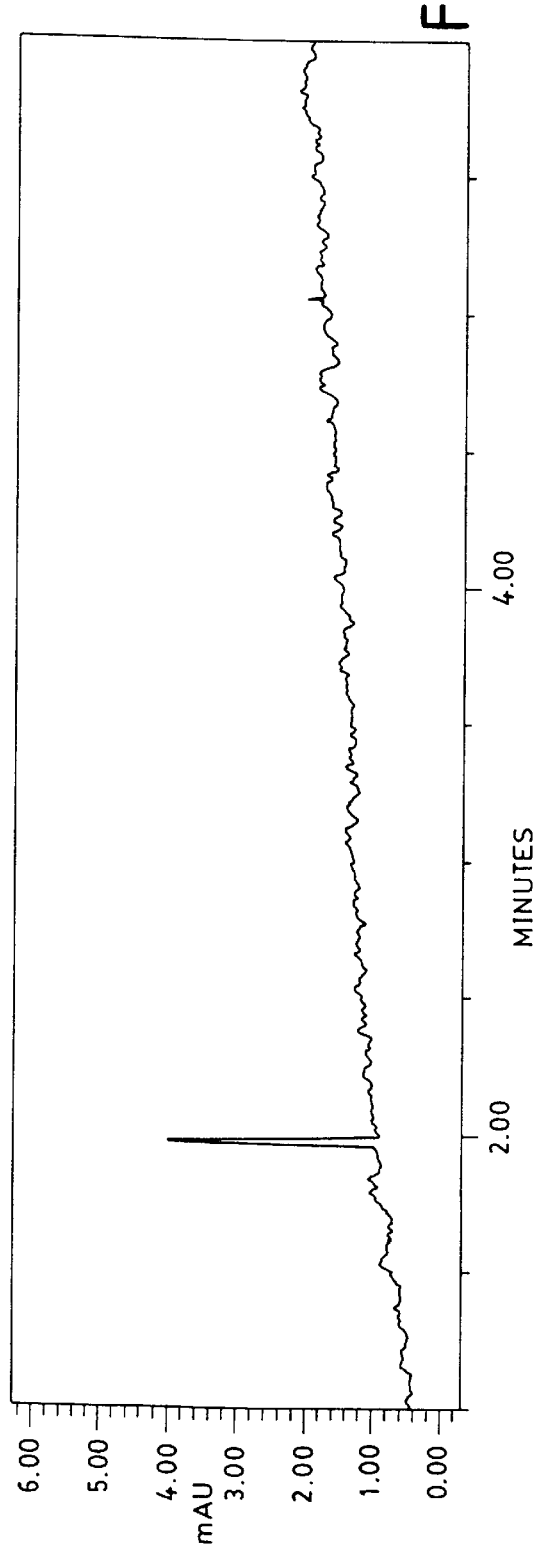
FIG.15A
FIG.15B

REAGENTS AND METHODS FOR PERFORMING ELECTROKINETIC CHROMATOGRAPHY

This application is a continuation in part of application Ser. No. 08/503,462, filed Jul. 18, 1995 now abandoned, and a continuation in part of application Ser. No. 08/585,049, filed Jan. 11, 1996 now abandoned.

1. FIELD OF THE INVENTION

The invention is in the field of electrokinetic chromatography. In particular, the invention is directed to reagents and methods of performing electrokinetic chromatography. The reagents and methods afford fast, high resolution separations with increased detectability.

2. DESCRIPTION OF THE PRIOR ART

Although a relatively new addition to the field of separations techniques, capillary electrophoresis ("CE") is already being used to separate a wide variety of solutes. Separations are performed in thin glass capillaries, as opposed to the 2-dimensional surfaces (such as gels or paper) which have traditionally been used in electrophoresis. CE has the ability to perform fast, high resolution separations in a simple experimental apparatus. Fast, high resolution separations result from the high efficiencies afforded by this technique.

High efficiency is obtained in CE because under ideal conditions, the sole source of band broadening is longitudinal diffusion (Jorgenson, J. W. and Lukas, K. D. Analytical Chemistry, 1981, (53) 1298–1302). Efficiency in separations systems is commonly expressed as theoretical plates (N). The larger the value of N, the higher the efficiency of the system. In capillary electrophoresis, under conditions where diffusion is the sole source of band broadening, the expression for N was derived by Jorgenson (Jorgenson, J. W. and Lukas, K. D.; supra):

$$N = \frac{\mu V l}{2DL} \qquad \text{equation 1}$$

where $\mu$ is the solute's apparent mobility, V is the applied voltage, l is the length of capillary from injection to detection, D is the solute's diffusion coefficient, and L is the total capillary length.

Equation 1 predicts that by increasing the applied voltage, higher efficiency (and therefore higher resolution) will be obtained. Furthermore, higher voltages cause the solute to move through the capillary at greater velocity, resulting in faster separation. Therefore, in theory, increasing the voltage will lead to faster analysis time and higher resolution. However, there is a limit to how high the voltage can be increased before resolution begins to degrade (Knox, J. H., Chromatographia, 26: 329–333 (1988); Grushka, E., McCormick, R. M. and Kirkland, J. J., Analytical Chemistry 61: 241–245 (1989). This limit occurs when the heat which is generated during application of the separation voltage causes thermal gradients in the capillary. These thermal gradients lead to band broadening and loss of resolution.

As the voltage increases, the current also increases, as defined by Ohm's Law:

$$V = IR \qquad \text{equation 2}$$

where V is the voltage, I is the current, and R is the electrical resistance of the capillary. Temperature gradients in the capillary are related to the heat generation rate or power density Q (Nelson, R. J., Paulus, A., Cohen, A. S., Guttinan, A. and Karger, B. L., Journal of Chromatography, 480: 111–127 (1989):

$$Q = \frac{VI}{\pi r^2 L} \qquad \text{equation 3}$$

where r is the capillary internal bore radius and L is the total capillary length. Thermal gradients exist when there is a difference in temperature between the buffer in the center of the capillary and the buffer near the wall. Since heat flows from warmer to cooler bodies, the temperature at the capillary wall will be lower because it is in contact with the cooler surrounding environment. Such temperature gradients lead to viscosity gradients within the capillary, with the viscosity being lowest in the center of the tube (where the buffer is warmest). Since the electrophoretic mobility of a solute is inversely proportional to the viscosity of the electrolyte, a solute molecule in the center of the tube will have a higher velocity than a solute molecule near the wall. This nonuniform velocity profile causes band broadening, which is detrimental to overall performance.

The difference in temperature between the center of the capillary and the wall can be calculated using equation 4 (Nelson, R. J. et al. supra):

$$\Delta T = \frac{Qr^2}{4K} \qquad \text{equation 4}$$

where K is the thermal conductivity of the electrolyte. Substituting equation 3 into equation 4 and substituting I with V and R using equation 2, the following equation 5 can be obtained:

$$\Delta T = \frac{V^2}{4\pi LR} \qquad \text{equation 5}$$

The capillary resistance is defined as (Nelson, R. J., et al. supra):

$$R = \frac{L}{\pi r^2 k} \qquad \text{equation 6}$$

where k is the electrical conductivity of the electrolyte. Substituting equation 6 into equation 7 leads to the final equation:

$$\Delta T = \frac{V^2 k r^2}{4L^2 K} \qquad \text{equation 7}$$

For a given electrolyte and capillary length, thermal gradients are proportional to the square of the capillary radius and the square of the applied voltage.

To maximize V (and therefore analysis speed and resolution) capillaries with very small internal diameters must be employed (i.e., 1 $\mu$m) to increase heat dissipation so that thermal gradients are not a substantial factor. However, small diameter capillaries lead to poor detectability when using on-column UV detection. The present state of the art in CE is to use capillaries with internal diameters of 50 or 75 $\mu$m to improve detection while keeping the band-broadening effect of the thermal gradients at an acceptable level.

Another way to reduce the deleterious effects of temperature gradients is to use electrolytes with low electrical conductivity (k). The most common electrolytes used in CE are prepared with inorganic salts as the buffering agents, such as sodium phosphate, sodium borate, etc. Because these salts dissociate completely in aqueous solution into highly mobile inorganic ions, the resulting electrolytes have high electrical conductivities. Lower concentrations of the salt can be used, but buffering capacity is reduced. Recently, the use of electrolytes prepared with zwitterionic buffers has gained acceptance in CE (Weinberger, R., "Practical Capillary Electrophoresis", Academic Press, San Diego, Calif., Chapter 2, pp. 37–39 (1993)). Such buffers have excellent capacities but low conductivities when used at their pI (where their net charge is zero). Using these buffers, large voltages can be applied for fast separations without the corresponding temperature gradients, band broadening, and subsequent resolution losses afforded by equivalent concentrations of non-zwitterionic buffers.

Electrokinetic chromatography (EKC), believed to be first reported by Terabe, is a subset of capillary elecirophoresis (Terabe, S., Otsuka, K, chikcawa, K., Tsuchiya, A. and Ando, T, Analytical Chemistry, 56: 111–113 (1984). In EKC, analytes partition between the bulk aqueous phase and an additive. EKC electrolytes consist of a buffering agent and an additive which can interact with the solutes. Additives which have been used in EKC include micelles (MEKC or MECC; Terabe, S. et al., supra), cyclodextrins (Terabe, S., Ozaki, H., Otsuka, K. and Ando, T., Journal of Chromatography, 332:211–217 (1985)), polymer ions (Terabe, S., Aemura, T., Analytical Chemistry, 62: 652–656 (1990)), and proteins (Yang, J. and Hage, D. S., Analytical Chemistry, 66: 2719–2725 (1994). Resolution of two analytes is achieved in EKC by one or both of the following mechanisms:

1) differences in their mobilities in the bulk aqueous phase (capillary zone electrophoresis), and/or
2) differences in their partitioning between the bulk aqueous phase and the additive, with the further requirement that the mobility of the analyte-additive complex is different from the mobility of the analyte in the bulk aqueous phase.

The second mechanism requires the existence of a "migration window" in EKC. The migration window is the length of time between the point in time at which a neutral species elutes with no partitioning ($t_o$), and the elution time of an analyte compound which completely partitions into the additive. For instance, MEKC is usually performed with sodium dodecyl sulfate (SDS) micelles. SDS micelles are anionic and have an electrophoretic mobility towards the anode. Uncoated fused silica capillaries are typically used in MEKC, and a bulk electroosmotic flow toward the cathode is produced at pHs >2.0. Above pH 6.0, the electroosmotic velocity is usually faster than the electrophoretic velocity of the SDS micelles, causing the micelles to have a net movement toward the cathode. This situation leads to a migration window, which for neutral analytes, is defined by the electroosmotic flow marker (no partitioning) and the micelle marker (complete partitioning). All neutral analytes must migrate between these two boundaries.

The existence of a migration window leads to an additional term in the resolution equation for MEKC compared to the standard resolution equation for chromatography. As developed by Terabe (Terabe, S., Otsuka, K. and Ando, T. Analytical Chemistry, 1985, (57) 834–841), the resolution equation for neutral analytes in MEKC is:

$$Rs = \left(\frac{N^{\frac{1}{2}}}{4}\right)\left(\frac{\alpha-1}{\alpha}\right)\left(\frac{k_2}{k_2+1}\right)\left(\frac{1-\frac{t_0}{t_{mc}}}{1+\frac{t_0}{t_{mc}}k_1}\right) \quad \text{equation 8}$$

where N is the theoretical plate count, a is the selectivity term, $k_1$ and $k_2$ are the capacity factors for the two analytes, $t_o$ is the electroosmotic flow time, and $t_{mc}$ is the micelle marker time.

The last term in equation 8 is known as the migration window term. Under conditions where the micelle and electroosmotic mobilities are directed toward the same electrode, reduction of the electroosmotic flow will lead to an increase in resolution. Therefore, MEKC electrolytes which lead to low electroosmotic flow are advantageous from a resolution standpoint.

The majority of MEKC separations have employed sodium dodecyl sulfate as the micelle forming agent. Like other forms of CE, the most common buffering agents are inorganic salts like sodium phosphate and sodium borate. Electrolytes prepared with these buffering agents are desirable from a resolution standpoint, since their high ionic strength reduces electroosmotic flow (Weinberger, R. supra). However, the electrolytes have high conductivity due to the high concentrations of mobile inorganic ions.

To perform fast, high resolution separations with such electrolytes, capillary internal diameters of 50 and 75 $\mu$m are employed. The tradeoff is lower detectability when using on-column UV detection. The use of 100 $\mu$m capillaries in MEKC has been shown to lead to detection limits and limits of quantitation ten times lower than with 75 $\mu$m capillaries when all other variables (i.e., injection time, voltage, etc.) are kept constant (Thomas, B. R., Wang, X G., Chen, X, Tyrrell, R.J and Ghodbane, S. Journal of Chromatography, 1994, (657) 383–394). The improvement was attributed to higher injected amount and increased path length with on-column UV detection. However, the improvement in detectability came at the price of some sacrifice in resolution.

MEKC electrolytes using SDS as the surfactant have been prepared with zwitterionic buffering agents such as 3-(cyclohexylamino)-1-propanesulfonic acid (CAPS) (Weinherger, R., Sappy, a,. and Moring, S., Journal of Chromatography, 1990, (516) 271–279). However, there is still a large concentration of sodium present from the SDS. Furthermore, electrolytes prepared with a zwitterionic buffer at a given concentration in MEKC have lower resolution than those prepared with the same concentration of an inorganic salt. The electroosmotic flow is much faster with low ionic strength electrolytes, so the migration window term in the resolution equation is decreased.

Cationic additives have also been used in EKC (Weinberger, R, vide supra). In the case of cationic surfactants, the EOF is reversed due to binding of such surfactants to the silica wall, generating a net positive charge. For EKC, such a reversal is favorable. The EOF moves toward the anode, while the cationic micelles, which want to move toward the cathode, move slowly toward the anode due to the reversed EOF. Therefore, a migration window is generated, which is bound by the EOF marker and the micelle marker. As with anionic additives, decreasing the EOF leads to a larger migration window and higher resolution.

The present state of the art of MEKC electrolytes is limited by the tradeoff which exists between good detectability and good separation performance. There is a need for an MEKC electrolyte that would allow large capillaries to be employed (i.e., 100 μm) for improved detectability and also allow the application of high voltages for fast, high resolution separations.

3. SUMMARY OF INVENTION

The present invention is directed to reagents and methods for performing electrokinetic chromatography. One embodiment of the present invention features a capillary electrophoresis reagent for isolating one or more analytes contained in a sample. The reagent comprises an aqueous phase for receiving said sample and forming a solution of said analyte. The aqueous phase has partitioning additive and buffering means. The partitioning additive is selected from the group consisting of surface active agents, cyclodextrins, polymer ions, and proteins. The partitioning additive is present in a concentration to effect partitioning of the analyte from solution. The buffering means in said aqueous phase is a polyamine for partitioning additives which are neutral to acidic and is a polycarboxylate for partitioning additives which are neutral to basic. Buffering means is at a concentration to maintain a pH of 2–7 when said aqueous phase is neutral to acidic and a pH of 7–12 when said aqueous phase is neutral to basic. The aqueous phase with said surface active agent and buffering means has a conductivity of 0.1 to 2.5 mS/cm.

Preferably, the aqueous phase has a conductivity of 0.5 to 2.0 mS/cm.

Preferably, the partitioning additive is a surface active agent. Where the partitioning additive is a surface active agent, the surface active agent is in said aqueous phase at a concentration sufficient to form one or more micelles. The surface active agent is an anionic surfactant for aqueous phases which are neutral to basic, and a cationic surfactant for aqueous phases which are neutral to acidic.

Preferably, anionic surfactants are selected from the group consisting of fatty acids having chain lengths of 8 to 20 carbons, long chain sulfonates, and alkyl aryl sulfonates. A particularly preferred anionic surfactant is selected from the group of chiral surfactants consisting of (S)-N-dodecoxycarbonylvaline, (S)-2-[(1-oxododecoxy)arnino]-3-methyl-1-sulfooxybutane, (R)-N-dodecoxycarbonylvaline, (S)-N-dodecoxycarbonyl-tert-leucine, (S)-N-tetradecoxycarbonylvaline, (S)-N-dodecoxycarbonylphenylglycine, (S)-N-dodecoxycarbonylserine, (S)-N-dodecoxycarbonylalanine, (S)-N-dodecoxycarbonylleucine, and (S)-N-dodecoxycarbonylproline.

Preferably, the cationic surfactant is selected from the group of surfactants consisting of long-chain amines and quaternary ammonium salts. A particularly preferred cationic surfactant is selected from the group consisting of tetradecyltrimethyl ammonium, cetylpyridinium, dodecyltrimethylammonium, and hexadecyltrimethylammonium.

Preferably, the polyamine has the following structural formula:

wherein
a is a numeral from about 1 to 8, and
R and R' are the same or different and may be alkyl, alkenyl or alkynyl substituents, branched or straight chain, substituted or unsubstituted, having from about 1 to 8 carbons, and may have one or more hydrophilic moities such as hydroxy, sulfhydryl, or amine. A particularly preferred polyamine is bis-tris propane.

Preferably the polycarboxylate is selected from the group consisting of succinnic acid, citric acid, cis-aconitic acid, isocitric acid, glutaric acid, fuimaric acid, malic acid, and oxaloacetic acid.

A further embodiment of the present invention comprises a kit for forming a electrokinetic reagent. The kit comprises means for forming an aqueous phase having one or more analytes in solution, a partitioning additive and a buffering means. The partitioning additive is selected from the group consisting of surface active agents, cyclodextrins, polymer ions, and proteins. The partitioning additive is present in a concentration to effect partitioning of the analyte from solution. The buffering means in the aqueous phase is present at a concentration to maintain a pH range of 2–7 for neutral to acidic aqueous phases and a pH range of 7–12 for neutral to basic aqueous phases. The buffering means is a polyamine for partitioning additives which are neutral to acidic and is a polycarboxylate for partitioning additives which are neutral to basic. The aqueous phase with said surface active reagent and buffering means has a conductivity of 0.1 to 2.5 mS/cm.

Preferably, the aqueous phase has a conductivity of 0.5 to 2.0 mS/cm.

Preferably, the partitioning additive is a surface active agent. Where the partioning additive is a surface active agent, the surface active agent is in said aqueous phase at a concentration sufficient to form one or more micelles. The surface active agent is an anionic surfactant aqueous phases which are neutral to basic, and a cationic surfactant for aqueous phases which are neutral to acidic Preferably, anionic surfactants are selected from the group consisting of fatty acids having chain lengths of 8 to 20 carbons, long chain sulfonates, and alkyl aryl sulfonates. And, even more preferred, the anionic surfactant is selected from the group of surfactants consisting of (S)-N-dodecoxycarbonylyvaline, (S)-2-[(1-oxododecoxy)amino]-3-methyl-1-sulfooxybutane, (R)-N-dodecoxycarbonylvaline, (S)-N-dodecoxycarbonyl-tert-leucine, (S)-N-tetradecoxycarbonylvaline, (S)-N-dodecoxycarbonylphenylglycine, (S)-N-dodecoxycarbonylserine, (S)-N-dodecoxycarbonylalanine, (S)-N-dodecoxycarbonylleucine, and (S)-N-dodecoxycarbonylproline.

Preferably, the cationic surfactant is selected from the group of surfactants consisting of long-chain amines and quaternary ammonium salts.

Preferably, the cationic surfactant is selected from the group consisting of tetradecyltrimethyl ammonium, cetylpyridinium, dodecyltrimethylammonium, and hexadecyltrimethylammonium.

Preferably, the polyamine has the following structural formula:

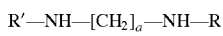

wherein
a is a numeral from about 1 to 8, and
R and R' are the same or different and may be alkyl, alkenyl or alkynyl substituents, branched or straight chain, substituted or unsubstituted, having from about 1 to 8 carbons, and may have one or more hydrophilic moities such as hydroxy, sulfhydryl, or amine. A particularly preferred polyarnine is bis-tris propane.

A preferred polycarboxylate is selected from the group consisting of succinnic acid, citric acid, cis-aconitic acid, isocitric acid, glutaric acid, fumaric acid, malic acid, and oxaloacetic acid.

A further embodiment of the presentation is a method for performing electrokinetic chromatography, the method comprises the steps of providing a capillary electrophoresis reagent for isolating analytes contained in a sample. The reagent comprises an aqueous phase having a partitioning additive and buffering means. The partitioning additive is selected from the group consisting of surface active agents, cyclodextrins, polymer ions, and proteins. The partitioning additive is present in a concentration to effect partitioning of analytes from solution. The buffering means has a concentration in the aqueous phase to maintain a pH of 2–7 for neutral to acidic aqueous phases and 7–12 for neutral to basic aqueous phases. The buffering means is a polyamine for partitioning additives which are neutral to acidic and a polycarboxylate for partitioning additives which are neutral to basic. The aqueous phase has a conductivity of 0.1 to 2.5 mS/cm. Next, a solution of said analyte in said aqueous phase is formed. And, such aqueous phase is injected into a capillary and a voltage imposed across the capillary to effect a separation of the analyte.

The reagents of the present invention may also comprise organic modifiers such as methanol, ethanol, propanol, acetonitrile and other typical solvents to alter the behavior of analyte in the aqueous phase.

These and other objects and advantages of the invention will become apparent in the following detailed description of the preferred embodiments, in conjunction with the drawings.

4. BRIEF DESCRIPTION OF THE DRAWINGS

FIG. 1 is the chemical structure of (S)-N-dodecoxycarbonylvaline, the surfactant used for the MEKC separations.

FIGS. 2A–B are chromatograms showing the separation of 1% (−)-ephedrine in the presence of (+)-ephedrine using 25 mM (S)-N-dodecoxycarbonylvaline and 25 mM $Na_2HPO_4$/25 mM $Na_2B_4O_7$, pH 8.5, in a 100 μm i.d. capillary, with hydrostatic injection times of 2 and 5 seconds.

FIGS. 3A–B are chromatograms showing the separation of 1% (−)-ephedrine in the presence of (+)-ephedrine using 25 mM (S)-N-dodecoxycarbonylvaline and 50 mM bis-tris propane, pH 8.5, in a 100 μm i.d. capillary, with hydrostatic injection times of 2 and 5 seconds.

Figure 6A:
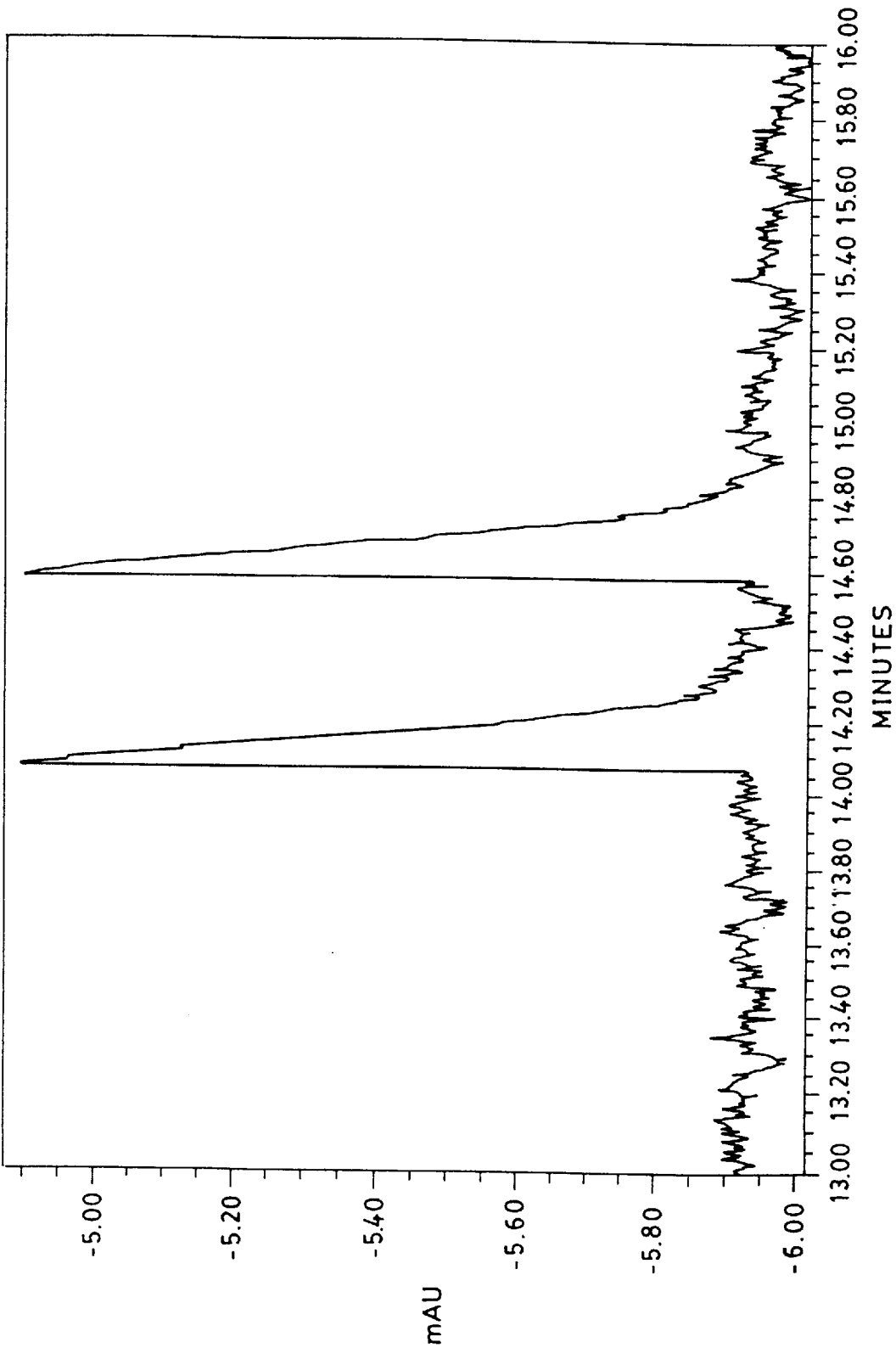

FIG. 6A is a chromatogram showing the separation of norephedrine enantiomers using 25 mM (S)-N-dodecoxycarbonylvaline and 25 mM $Na_2HPO_4$/25 mM $Na_2B_4O_7$, pH 8.5, in a 50 μm i.d. capillary with 15 kV applied voltage.

FIG. 6B is a chromatogram showing the separation of norephedrine enantiomers using 25 mM (S)-N-dodecoxycarbonylvaline and 50 mM bis-tris propane, pH 8.5, in a 50 μm i.d. capillary with 15 kV applied voltage.

Figure 7:
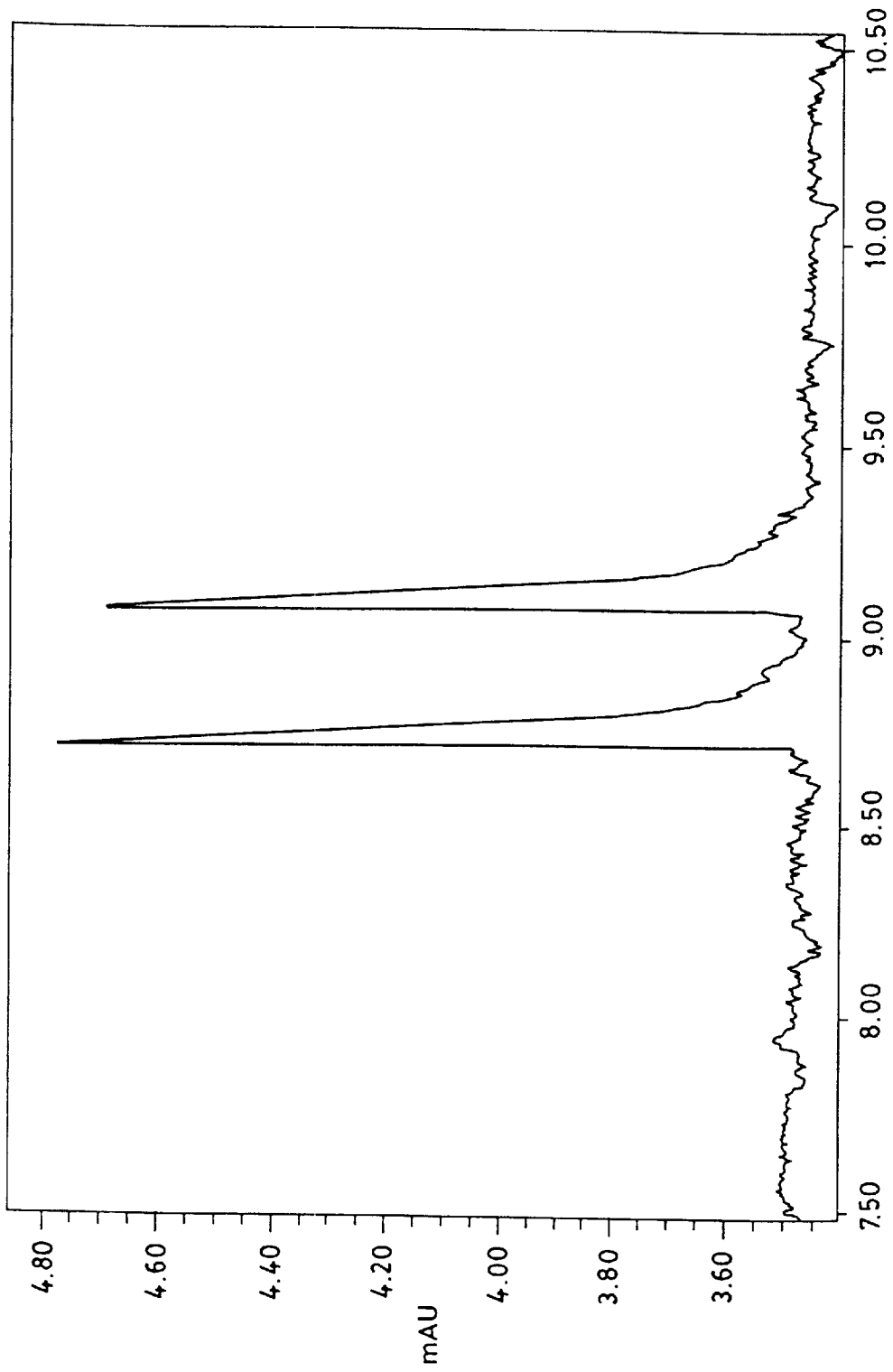

FIG. 7 is a chromatogram showing the separation of norephedrine enantiomers using 25 mM (S)-N-dodecoxycarbonylvaline and 50 mM bis-tris propane, pH 8.5, in a 50 μm i.d. capillary with 30 kV applied voltage.

FIG. 8 are the chemical structures of polyamines other than bis-tris propane demonstrated to be useful in this invention.

Figure 9:
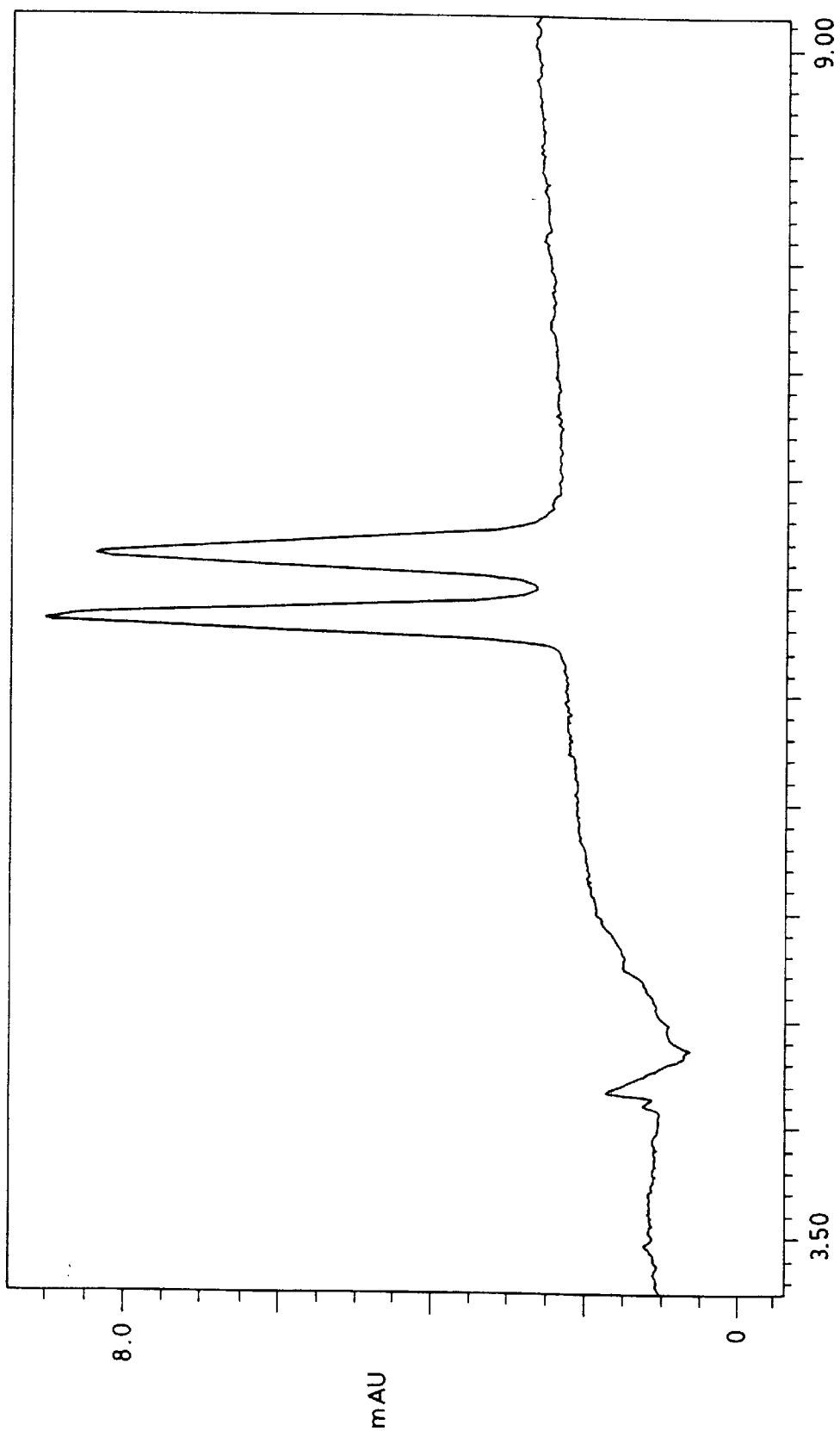

FIG. 9 is a chromatogram showing the baseline separation of metoprolol enantiomers and was obtained using an electrolyte containing 25 mM (S)-N-dodecoxycarbonylvaline and 25 mM N,N'-bis(2-aminoethyl)-1,3-propanediamine.

Figure 10:
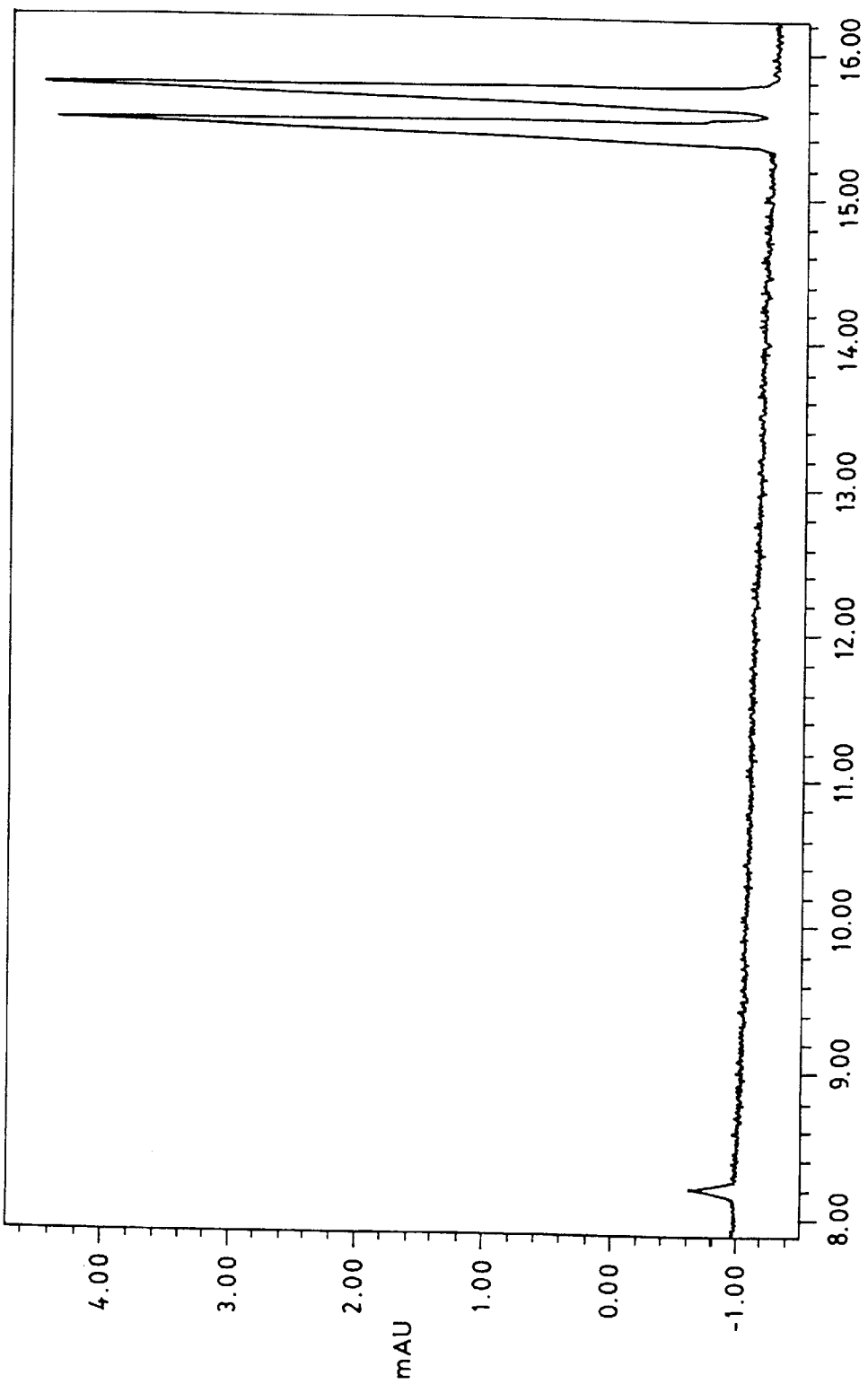

FIG. 10 is a chromatogram showing the baseline separation of benzoin enantiorners and was obtained using an electrolyte containing 25 mM (S)-N-dodecoxycarbonylvaline and 50 mM pentrol.

Figure 11:
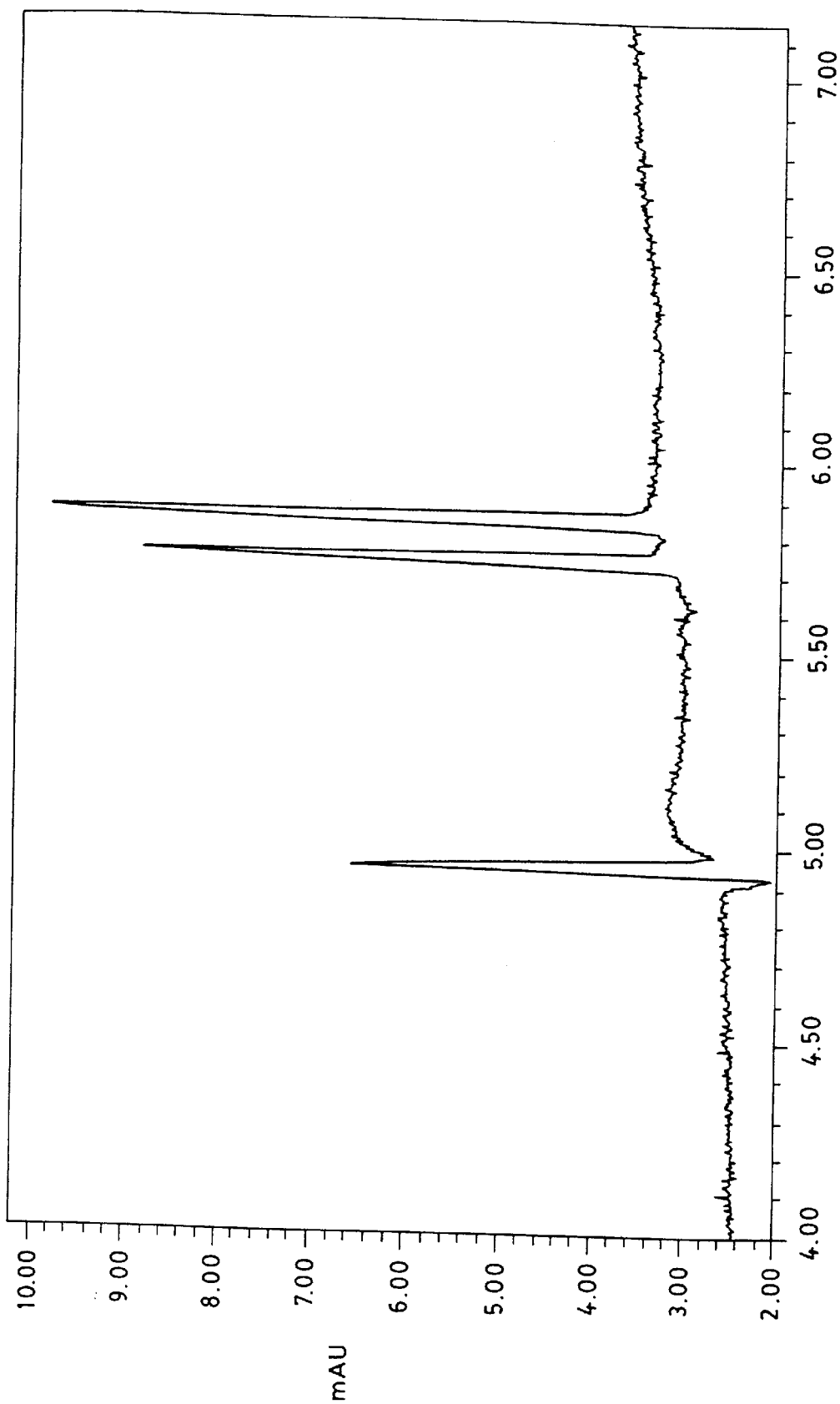

FIG. 11 is a chromatogram showing the baseline separation of norphenylephrine enantiomers and was obtained using an electrolyte containing 25 mM (S)-N-dodecoxycarbonylvaline and 15 mM pentaethylenehexamine.

Figure 12:
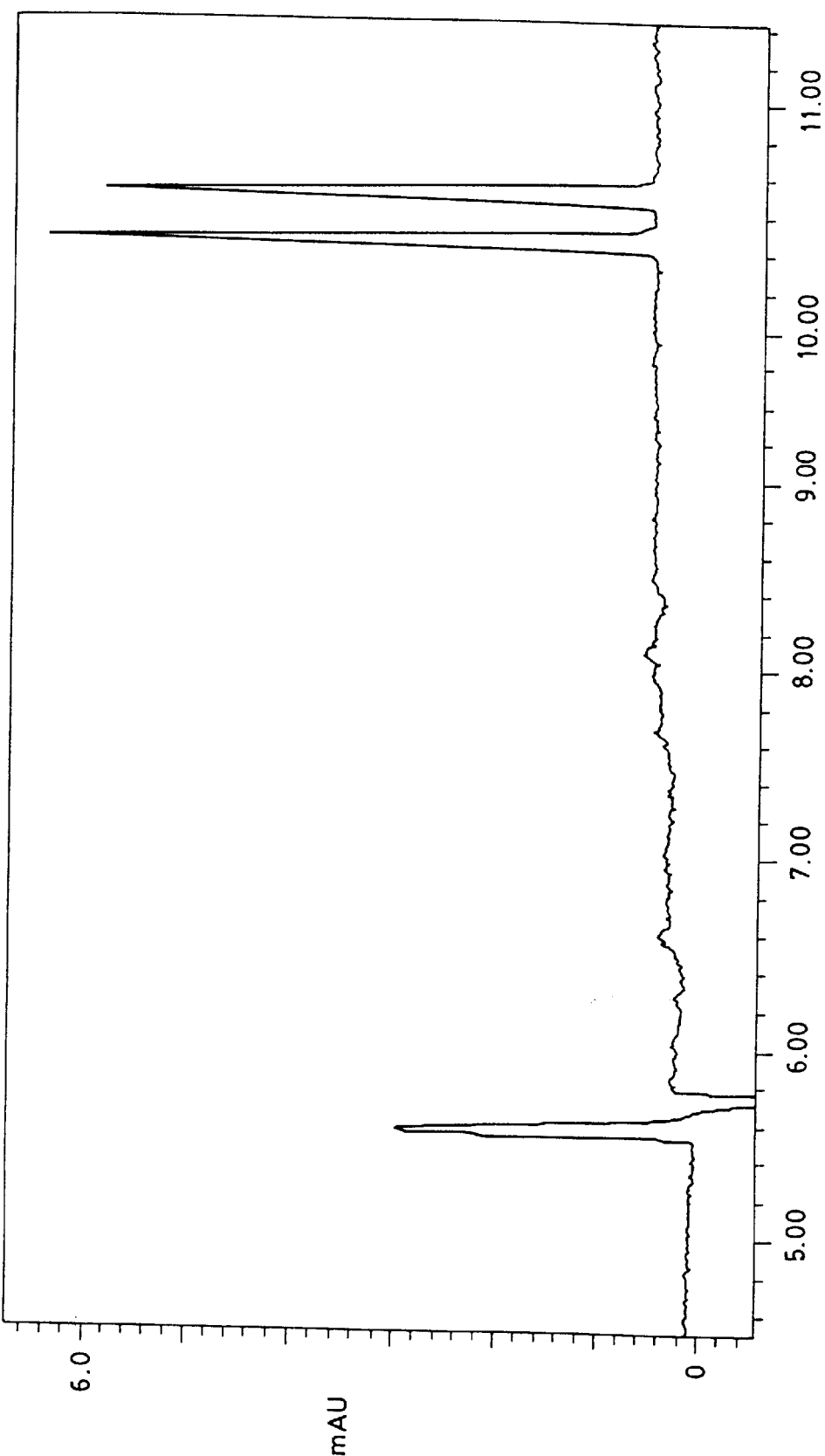

FIG. 12 is a chromatogram of the baseline separation of metoprolol enantiomers and was obtained using an electrolyte containing 25 mM (S)-N-dodecoxycarbonylvaline and 20 mM 4,7,10-trioxa-1, 13-tridecanediamine.

Figure 13:
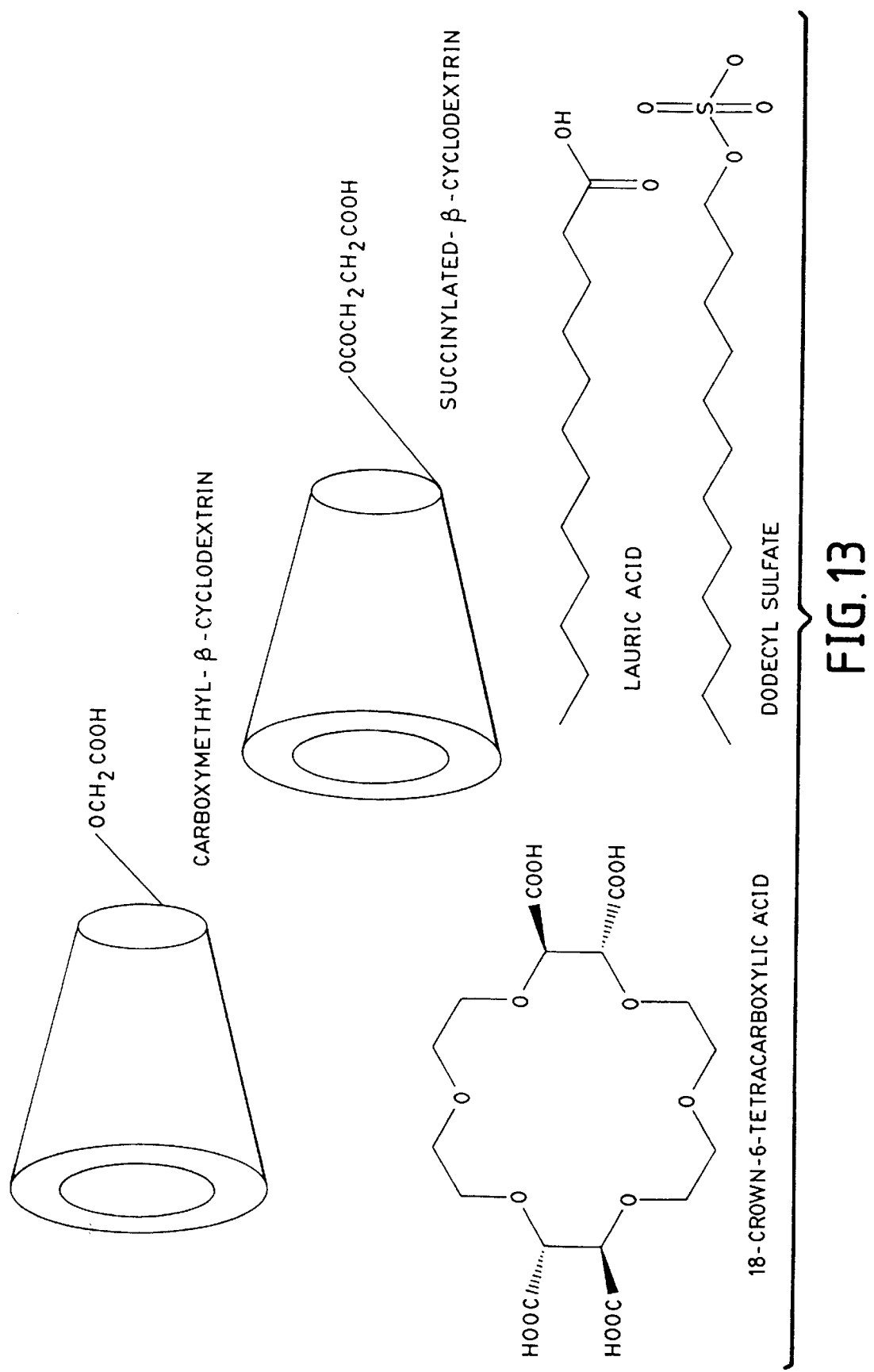

FIG. 13 is the chemical structures of the additives, which include two anionic cyclodextrin derivatives (carboxymethylated-β-cyclodextrin and succinylated-β-cyclodextrin), a chiral crown ether (18-crown-6-tetracarboxylic acid), and two achiral surfactants (lauric acid and dodecyl sulfate).

FIG. 14A is a chromatogram of the separation of the enantiomers of verapamil and was obtained using an electrolyte containing 0.1% (w/v) carboxymethyl-β-cyclodextrin and 25 mM bis-tris propane.

FIG. 14B is a chromatogram of the separation of the enantiomers of verapamil and was obtained using an electrolyte containing 0.1% (w/v) carboxymethyl-β-cyclodextrin and 25 mM sodium tetraborate.

FIG. 15A is a chromatogram of the separation of the enantiomers of verapamil and was obtained using an electrolyte containing 0.1% (w/v) succinylated-β-cyclodextrin and 25 mM bis-tris propane.

FIG. 15B is a chromatogram of the attempted separation of the enantiomers of verapamil and was obtained using an electrolyte containing 0.1% (w/v) succinylated-β-cyclodextrin and 25 mM sodium tetraborate.

Figure 16A:
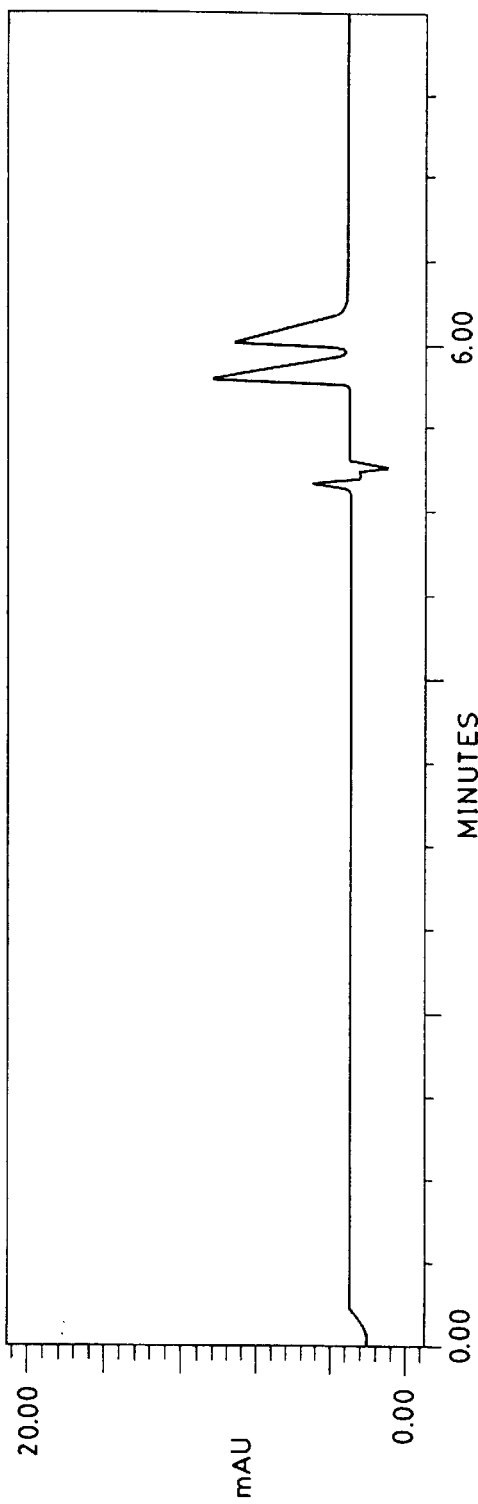

FIG. 16A is a chromatogram of the separation of the enantiomers of methylbenzylamine, resolution of 1.5 was obtained using an electrolyte containing 5 mM 18-crown-6-tetracarboxylic acid and 25 mM bis-tris propane.

Figure 16B:
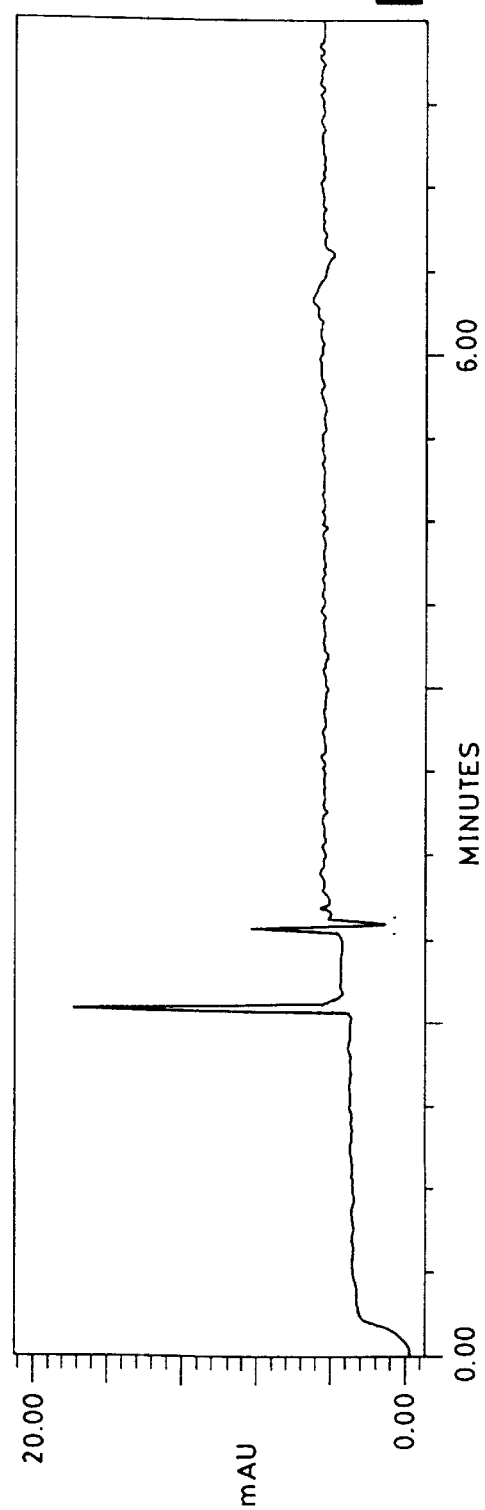

FIG. 16B is a chromatogram of the attempted separation of the enantiomers of methylbenzylamine, and was obtained using an electrolyte containing 5 mM 18-crown-6-tetracarboxylic acid and 25 mM sodium tetraborate.

Figure 17:
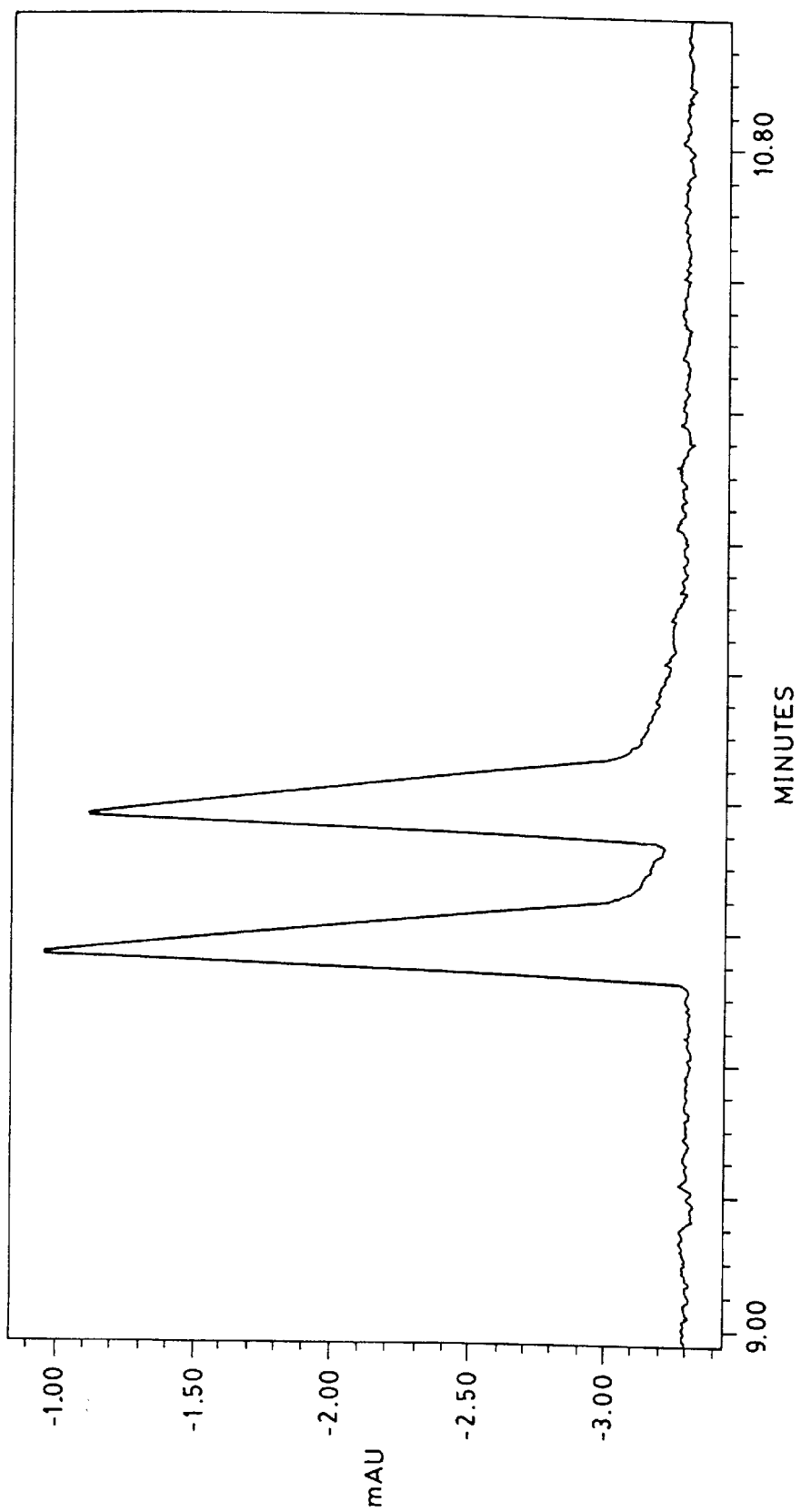

FIG. 17 is a chromatogram showing the baseline separation of the diastereomers of nadolol using an electrolyte containing 25 mM lauric acid and 50 mM bis-tris propane, pH adjusted to 8.5 with phosphoric acid.

Figure 18:
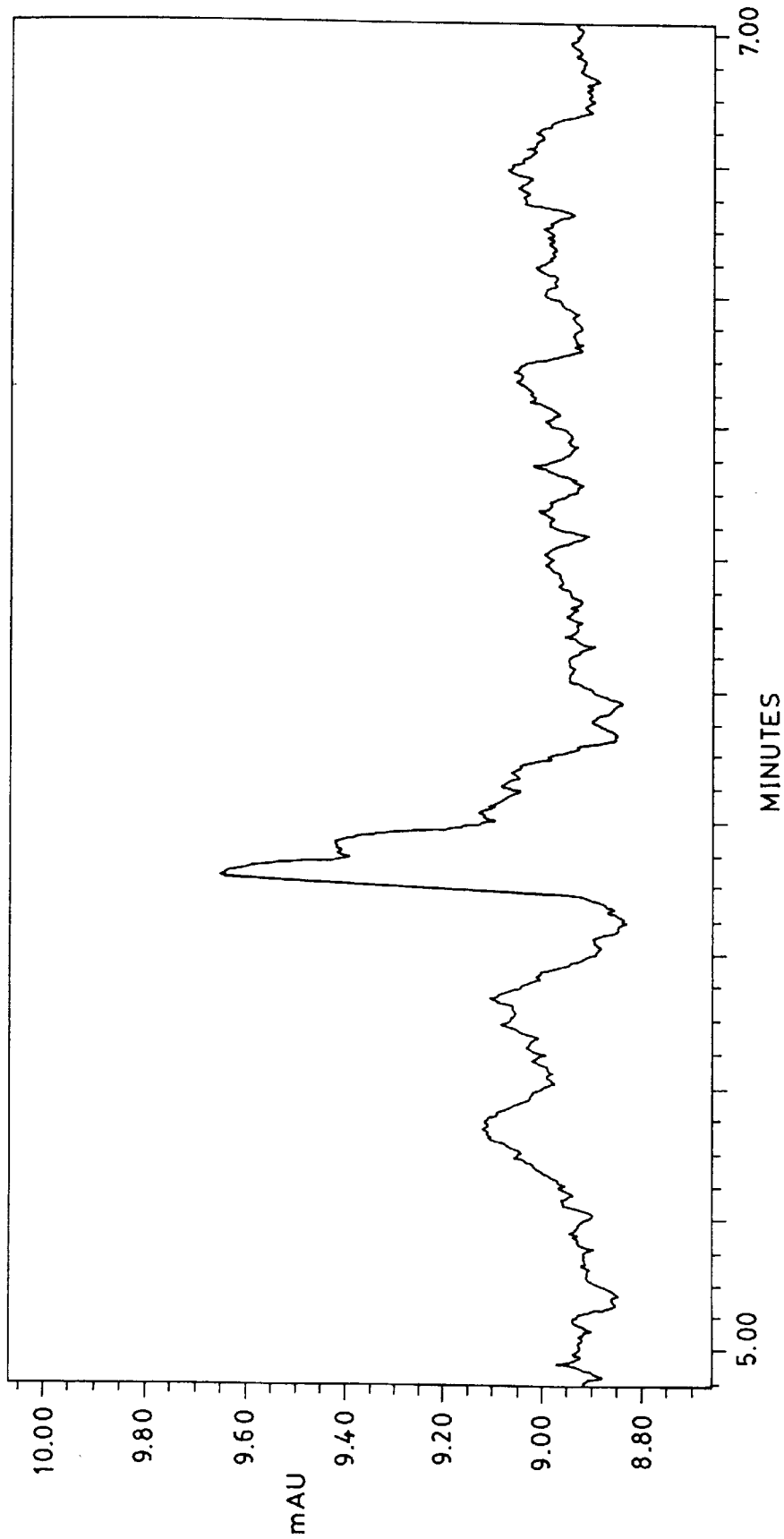

FIG. 18 is a chromatogram that shows no separation for the diastereomers of nadolol, and was obtained with an electrolyte containing 25 mM lauric acid, 25 mM disodium phosphate/25 mM sodium tetraborate, pH 8.5 with phosphoric acid.

Figure 19:
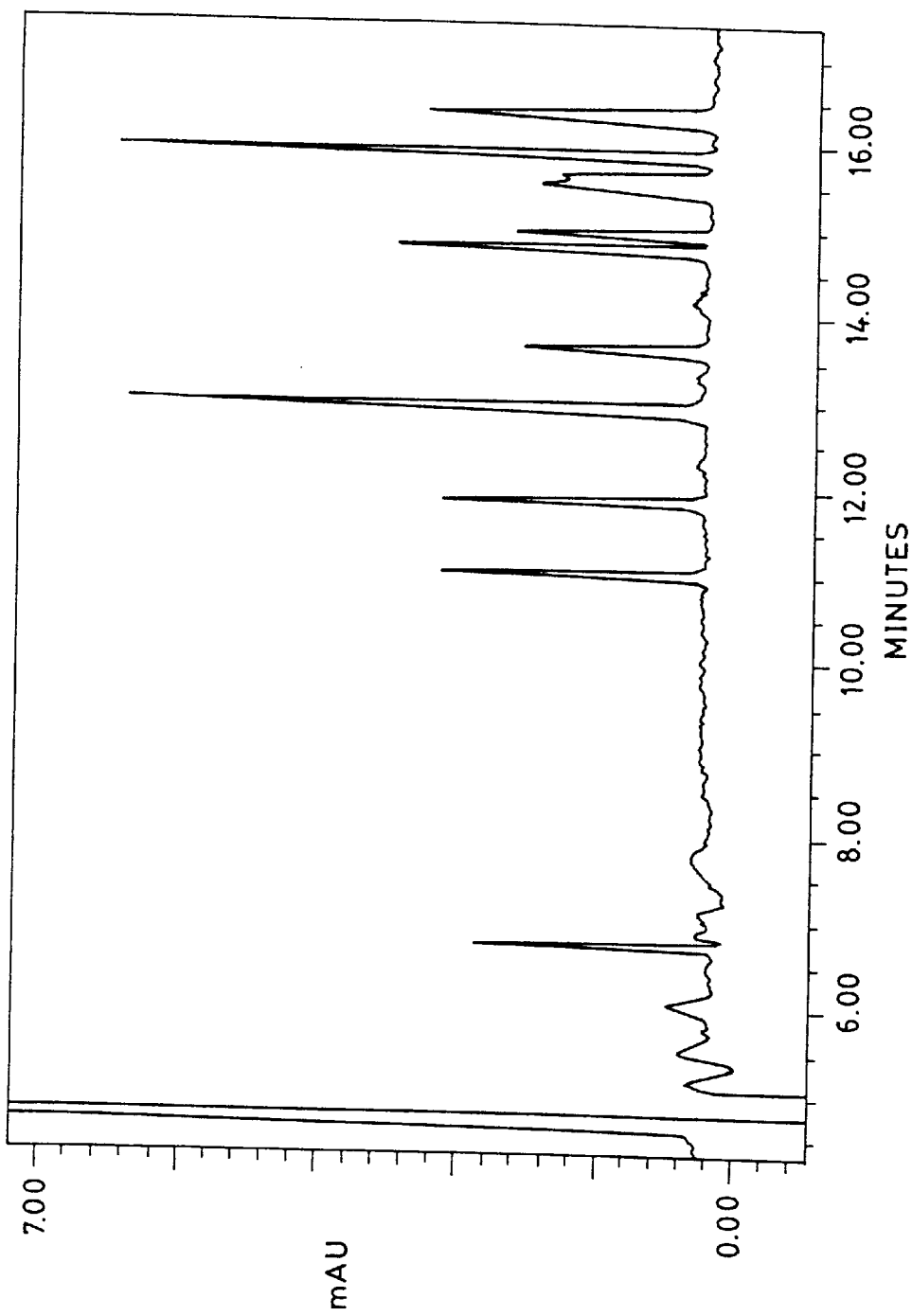

FIG. 19 is a chromatogram showing the separation of eleven priority pollutant phenols using an electrolyte containing 43 mM protonated dodecylsulfate and 43 mM bis-tris propane, pH 8.6 (unadjusted).

Figure 20:
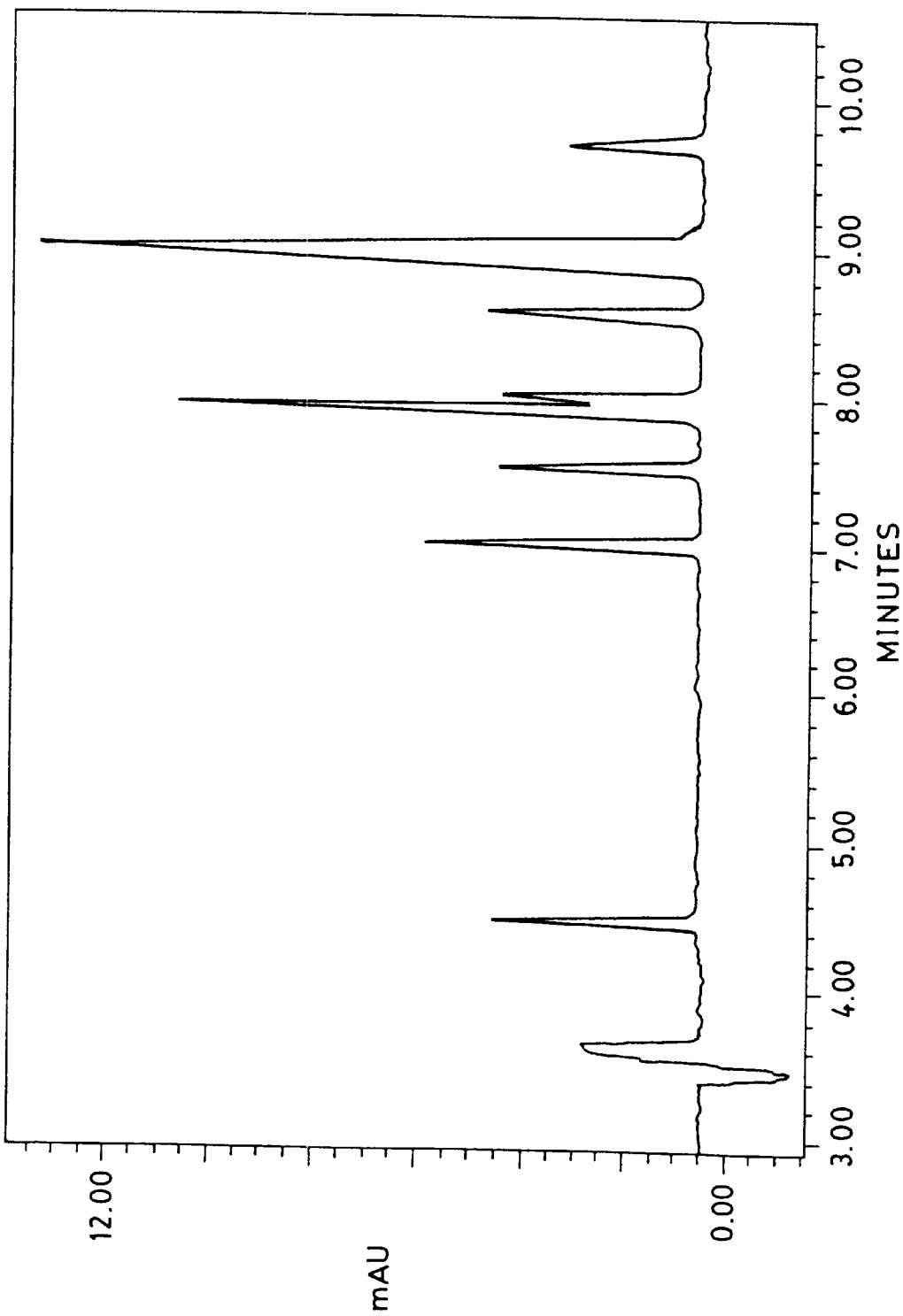

FIG. 20 is a chromatogram showing the separation of the same sample using an electrolyte containing 43 mM sodium dodecylsulfate and 21.5 mM disodium phosphate/21.5 mM sodium tetraborate, pH adjusted to 8.6 with phosphoric acid.

Figure 21:
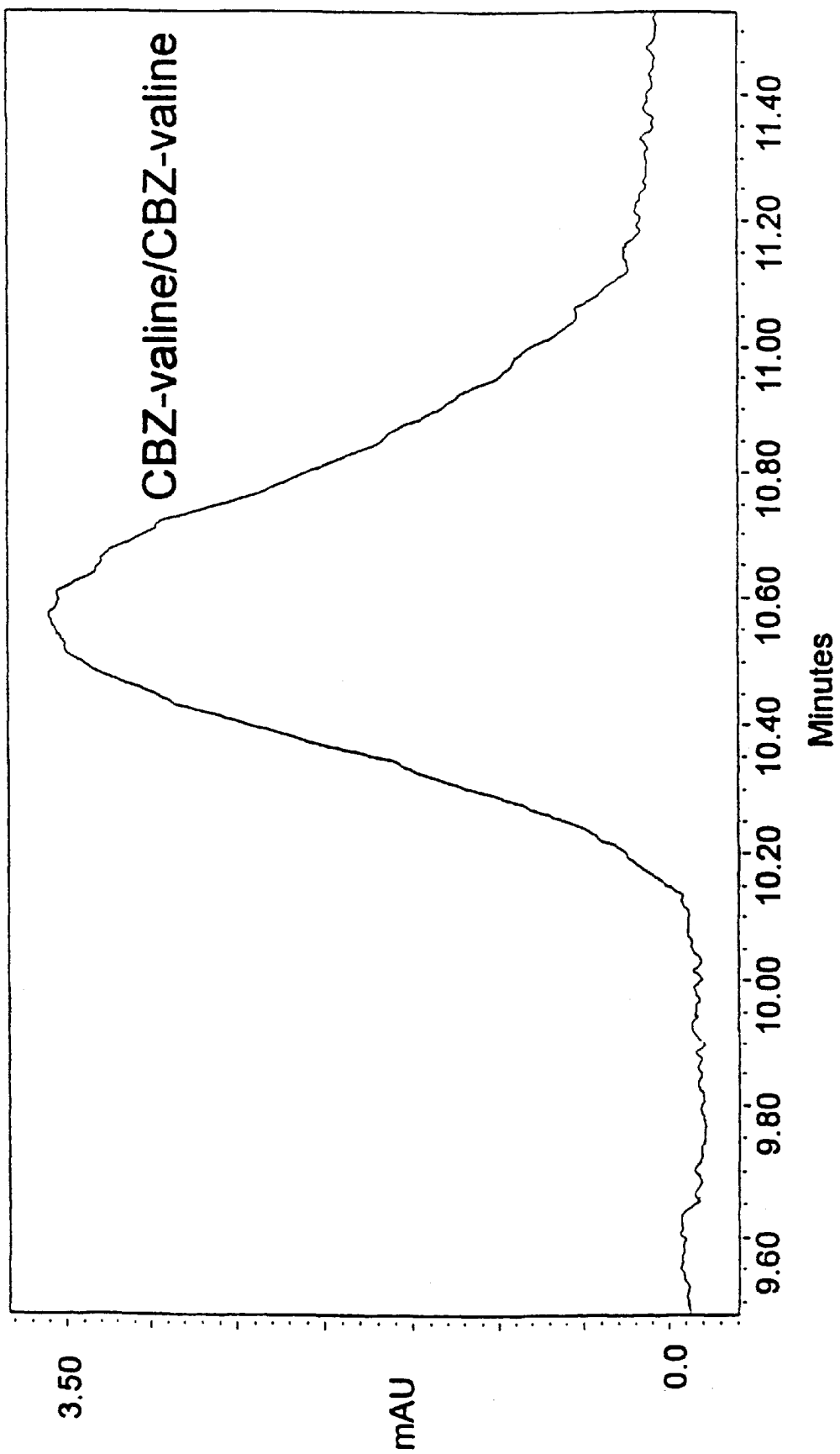

FIG. 21 shows the separation of CBZ-valine and CBZ-norvaline using an electrolyte comprised of 20 mM tetradecyltrimethylammonium hydroxide/25 mnM NaH$_2$PO$_4$, pH 3.0.

Figure 22:
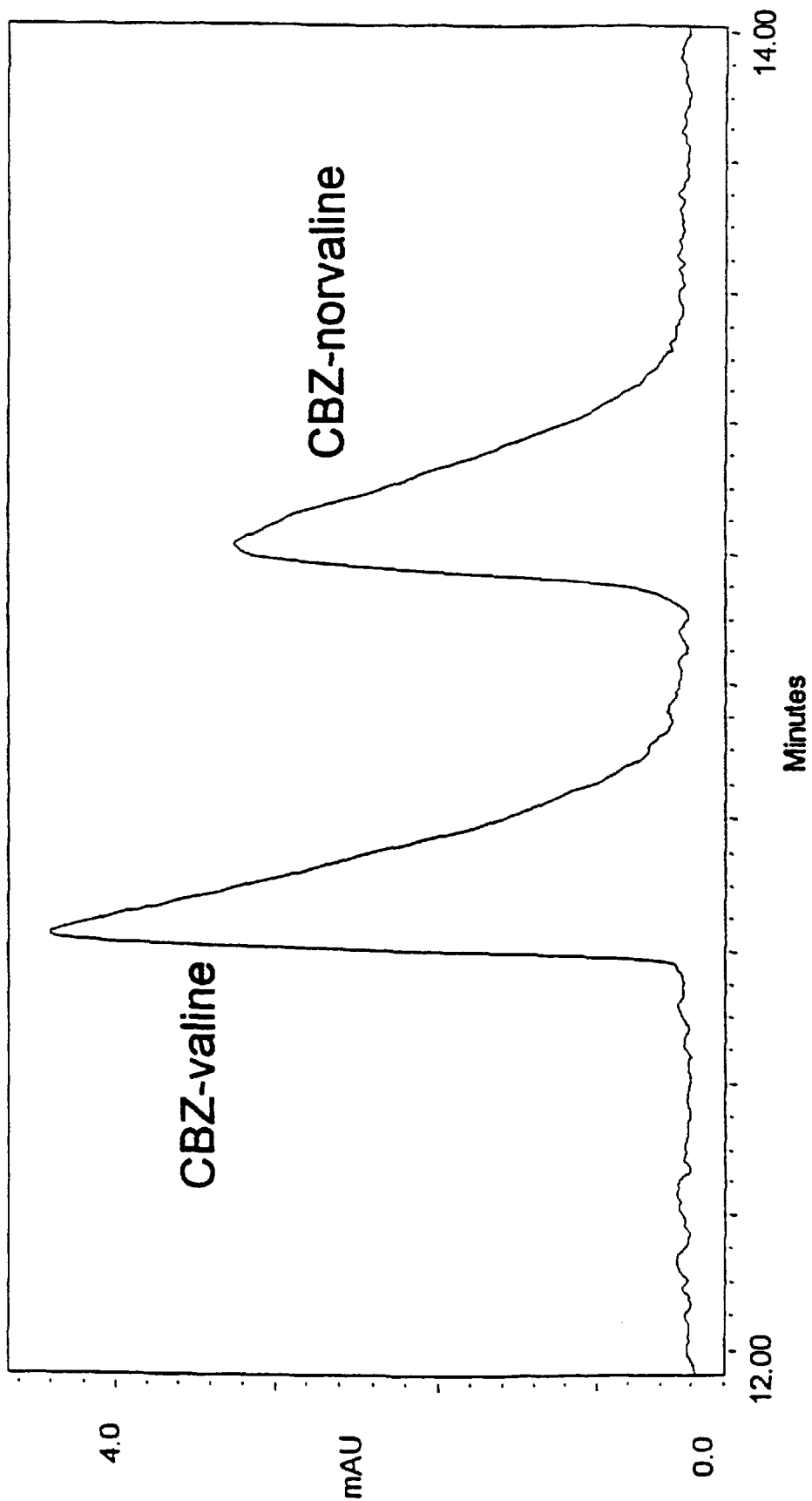

FIG. 22 shows the separation of CBZ-valine and CBZ-norvaline using an electrolyte comprised of 20 mM tetradecyltrimethylammonium hydroxide/25 mM citric acid, pH 3.0.

Figure 23:
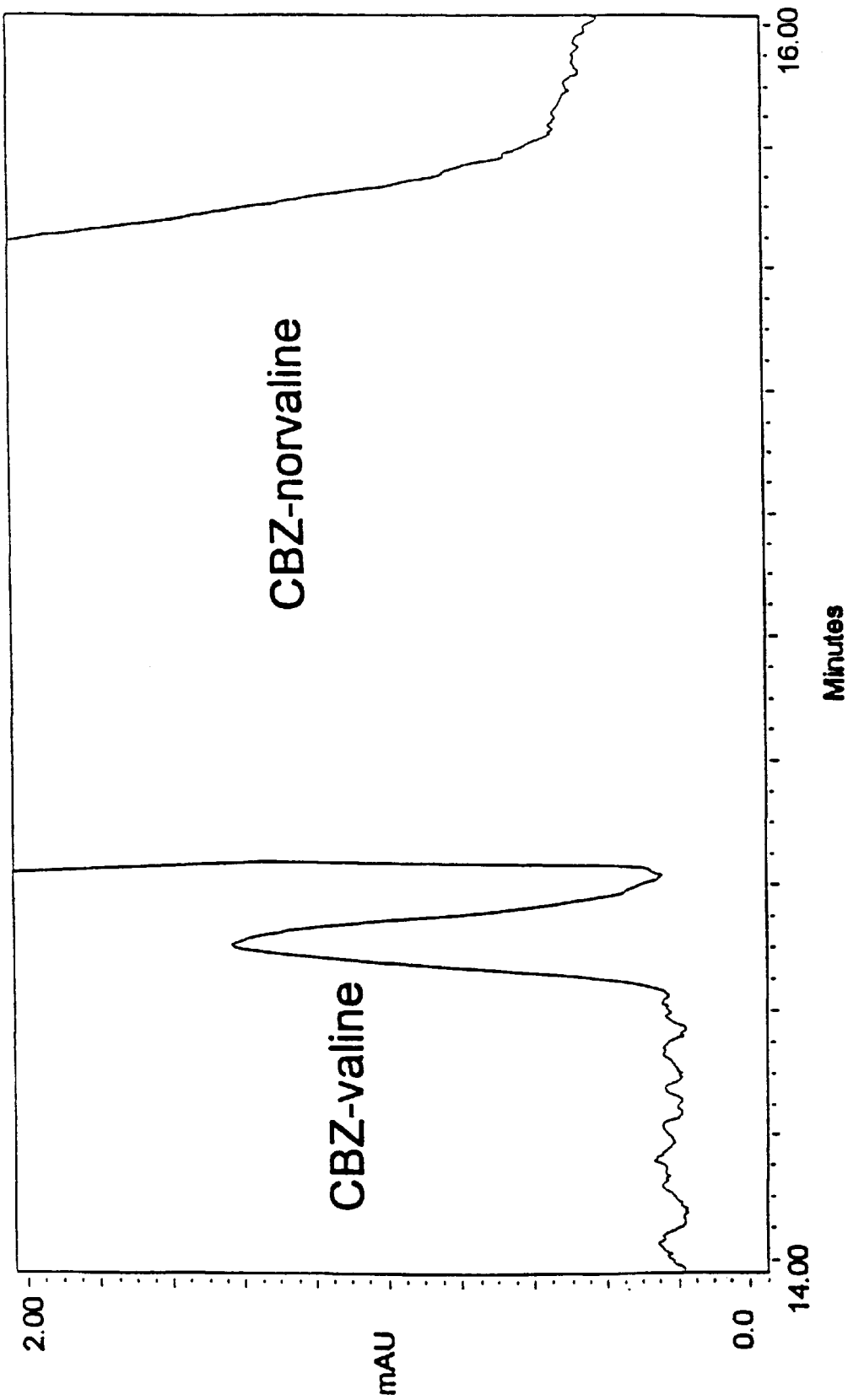

FIG. 23 shows the separation of CBZ-norvaline contaminated with 1% CBZ-valine norvaline using an electrolyte comprised of 20 mM tetradecyltrimethylammonium hydroxide/25 mM citric acid, pH 3.0.

5. DETAILED DESCRIPTION OF THE INVENTION

In the present invention, electrolytes are prepared with anionic EKC additives in the protonated form (as opposed to the conjugate base salt form) and free polyamino (as opposed to the conjugate acid salt form) compounds as the buffering agent. These EKC buffer/additive combinations are characterized by low conductivity, since there are no highly mobile inorganic ions present. Furthermore, the electroosmotic flow is low since these free polyamines greatly reduce it. Surprisingly, separations can be performed at higher voltages in larger internal diameter capillary columins than are typically used in EKC. Higher resolution is obtained because of the higher voltages and lower electroosmotic flow, and greatly improved detectability is realized because of the capillary column's larger internal diameter.

Figure 1:
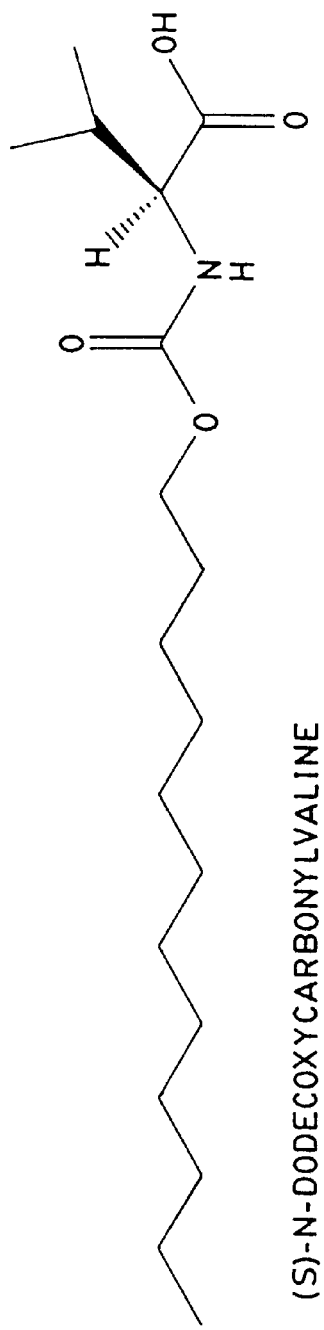

FIG. 1 is a structural formula depiction of a preferred embodiment of the invention, the anionic chiral surfactant additive class which was used in some of the separations which follow, specifically (S)-N-dodecoxycarbonylyvaline, described further in U.S. patent application Ser. No. 08/124,681, filed Sep. 20, 1993, and PCT/US94/10655, filed Sep. 20, 1994, both of which are incorporated herein by reference. This surfactant contains a carboxylate head group and is fully anionic at pHs above 6.5. The surfactant is used in its protonated form, and is available from Waters Corporation, 34 Maple St., Milford, Mass. 01757. A short list of other chiral surfactants disclosed in both applications cited immediately above includes, but is not limited to: (S)-2-[(1-oxododecoxy) amino]-3-methyl-1-sulfooxybutane; (R)-N-dodecoxycarbonylvaline; (S)-N-dodecoxycarbonyl-tert-leucine; (S)-N-tetradecoxycarbonylvaline; and (S)-N-dodecoxycarbonylphenylglycine; (S)-N-dodecoxycarbonylserine, (S)-N-dodecoxycarbonylalanine, (S)-N-dodecoxycarbonylleucine, and (S)-N-dodecoxycarbonylproline.

However, the electrolyte combination of protonated additive and buffer is not limited to chiral surfactants as additives, but may also be used in combination with other protonated EKC additives such as carboxylic and sulfonic acid derivatives of: cyclodextrin; macrocyclic antibiotics (e.g. vancomycin); achiral and chiral synthetic surfactants (examples given above); achiral and chiral polymers; and biomolecules (e.g. amino acids, peptides, proteins, oligosaccharides, nucleic acids, oligonucleotides, etc.).

In examples 8–11, polyamines other than bis-tris propane (structures given in FIG. 8) were used in combination with (S)-N-dodecoxycarbonylvaline to resolve the enantiomers of several chiral compounds with low EOF and wattage. These examples illustrate that electrolytes with low EOF and wattage can be obtained with (S)-N-dodecoxycarbonylvaline in combination with a variety of polyamines, i.e., the invention is not limited to bis-tris propane. It should be apparent to those skilled in the art that improved detectability would be obtained when using the surfactant with these polyamines vs. inorganic buffers.

Figure 5:
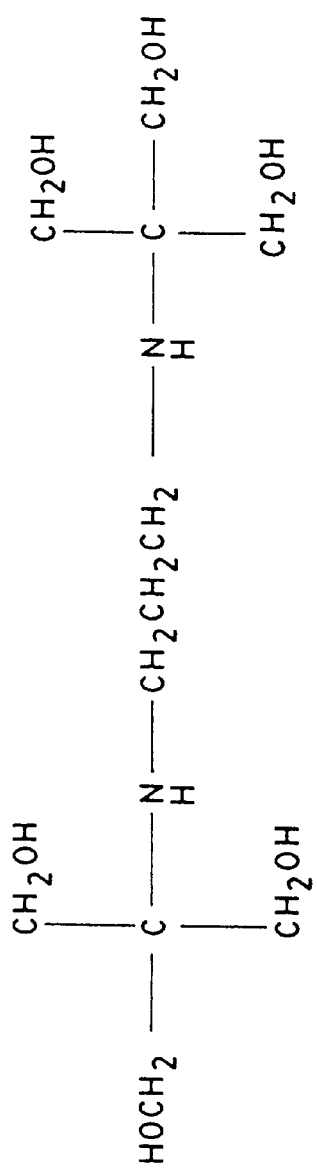
FIG. 5 is the chemical structure of bis-tris propane.

Specifically with reference to the additive/polyarnine buffer combination of a diamine and a chiral surfactant, their structures are disclosed in FIGS. 1 and 5. FIG. 1 is the structural formula of the protonated chiral surfactant (S)-N-dodecoxycarbonylvaline. In solution the chiral surfactant will form micelles above its critical micellar concentration (cmc), the outer periphery of the micelle presenting the anionic portion of the head group to the aqueous environment. The charged anionic head group of the surfactant will give up its proton to a more basic amine, and so will be present in its charged form. In a preferred embodiment, the polyamine used herein is bis-tris propane (FIG. 5), a diamine buffer that is available as the free amine. The pKas of the two amine moieties of the diamine are 6.8 and 9.0, respectively. It has good buffering capacity over the pH range of 6.3–9.5. When dissolved in water, bis-tris propane causes the pH to increase since it is a base. The additive surfactant, which is in the acid form, donates its proton to the solution, causing the pH of the solution to decrease. It is hypothesized that a complex forms comprising the negatively-charged anionic surfactant and the positively charged polyamine. By choosing the proper concentration ratio of bis-tris propane to (S)-N-dodecoxycarbonylvaline, which is well within the skill of one of ordinary skill in the art, an electrolyte pH which is within the buffering range of bis-tris propane can be achieved. The conductivity of the resulting electrolyte is lower than that afforded by electrolytes prepared with inorganic buffers, because there is no contribution from the inorganic counterions prevalent in salts, such as sodium or chloride. It was surprising to find that the electrolyte used in the chromatograms of FIGS. 3 and 4, despite the adjustment of pH with phosphoric acid, could be used at high field strength in 100 μm capillaries with minimal joule heat generated.

Another benefit of bis-tris propane when used with protonated additives in EKC is that the electroosmotic flow ("EOF") is reduced, and it has been shown previously that diamino compounds alone reduce the electroosmotic flow in untreated fused silica capillaries (Landers, J. P., Oda, R. P., Madden, B. J. and Spelsberg, T. C. Analytical Biochemistry, 1992, (205) 115–124; Song, L., Ou, Q. and Yu, W. Journal of Chromatography, 1993, (657) 175–183). However, it is surprising that detection limits can be significantly reduced (a full order of magnitude) as a result of both the low conductivity afforded by these buffer/additive combinations, and as well as the increase in resolution due to the EOF reduction. Both factors contribute to the ability to use greater quantities of analyte for improved sensitivity. This simultaneous improvement in 1) resolution and 2) lowered conductivity results in a synergistic improvement in sensitivity, demonstrated herein.

To demonstrate that the advantages of polyamine buffers in EKC are not limited to (S)-N-dodecoxycarbonylvaline, bis-tris propane was used in combination with several other EKC additives. The resulting electrolytes were compared to ones generated with the same additive in combination with inorganic buffers, and are shown in Examples 12–16. Note that for all additives the electrolyte prepared with bis-tris propane offered superior resolution and substantially lower wattage. The additives include two anionic cyclodextrin derivatives (carboxymethylated-β-cyclodextrin and succinylated-β-cyclodextrin, examples 12-13), a chiral crown ether (18-crown-6-tetracarboxylic acid, example 14), and two a chiral surfactants (lauric acid and dodecyl sulfate, examples 15-16). All of these anionic additives, with the exception of dodecyl sulfate, are commercially available in the protonated form. Chemical structures of the additives are given in FIG. 13. At the end of this section is a table summarizing the results for each additive with bis-tris propane and the inorganic buffer.

Other polyamine compounds may also come within the spirit and scope of this invention. For instance, many amines are available commercially that could be used to gain the effect demonstrated herein. Such compounds include, but are not limited to: ethylenediamine; 1,3-diaminopropane; 1,2-diaminopropane; 1,4-diaminobutane; 1,2-diamino-2-methylpropane; (+/−)-1,3-diaminopentane; 1,5-diaminopentane; 2,2-dimethyl-1,3-propanediamine; 1,6-hexanediamine; 2-methyl-1,5-pentanediamine; 1,7-diaminoheptane; 1,8-diaminoctane; 1,9-diaminononane; 1,10-diaminodecane; 1,12-diaminododecane; n-methyl ethyl enedi amine; n-ethylethylenediamine; n-propylethylenediamine; n-isopropylethylenediamine; n,n-dimethylethylenediamine; n,n-diethylethylenediamine; n,n-diisopropylethylene diamine; n,n-dibutylethylenediamine; n,n,n-trimethylethylenediamine; n,n-dimethyl-n'-ethylethylenediamine; n,n-diethyl-n'-methylethylenediamine; n,n,n-triethylethylenediamine; n,n,n,n-tetramethylethylenediamine; n,n,n,n-tetraethylethylenediamine; n-methyl-1,3-propanediamine; n-propyl-1,3-propanediamine; n-isopropyl-1-3-propanediamine; 3-dimethylaminopropylamine; 3-diethylaminopropylamine; 3-(dibutylamino)propylamine; n,n'-dimethyl-1,3-propanediamine; n,n'-diethyl-1,3-propanediamine; n,n'-diisopropyl-1,2-propanediamine; n,n,n'-trimethyl-1,3-propanediamine; n,n,n,n'-tretramethyl-1,3-propanediamine; n,n,n,'n'-tetraethyl-1,3-propanediamine; n,n,n,'n'-tetramethyl-1,3-butanediamine; n,n, 2,2-tetramethyl-1,3-propanediaamine; n,n,n,'n'-tetramethyl-1,4-butanediamine; 2-amino-5-diethylaminopentane; n,n'-dimethyl-1-6-hexanediaamine; n,n,n,'n'-tetramethyl-1,6-hexanediamine; tris(dimethylarnino)methane; diethylenetriamine; n,n,n,'n,n'-pentamethyldiethylenetriamine; n-(2-aminoethyl)-1,3-propanediamine; 3,3'-diamino-n-methyldipropylamine; 3,3'-iminobispropylamine; 3,3'-iminobis(n,n-dimethylpropylamine); spermidine; bis(hexamethylene) triamine, triethylenetetramine; 1,1,4,7,10,10-hexamethyltriethylenetetramine; n,n'-bis(3-aminopropyl)-ethylenediamine; n,n'-bis(2-aminoethyl)-1,3-propanediamine; n,n'-bis(3-aminopropyl)-1,3-propanediamine; spermine; tris(2-aminoethyl)amine; tetraethylenepentamine; pentaethylenehexamine; 5-amino-2,2,4-trimethyl-1-cyclopentanemethylamine mixture of isomers; 4,4'-methylenebis(cyclohexylamine); 4,4'-methylenebis(2-methylcyclohexylamine); 1,2-diaminocyclohexane; cis-1,2-diaminocyclohexane; (+/−) trans-1-2-diaminocyclohexane; (1S,2S)-(+)1,2-diaminocyclohexane; (1R,2R)-(−)-1,2-diaminocyclohexane; trans-1,4-diaminocyclohexane; 1,3-cyclohexanebis-(methylamine); n-cyclohexyl-1-3-propanediamine; 1,8-diamino-p-menthane; n,n'-diethyl-2-butene-1,4-diaamine; n,n,n',n'-tetramethyl-2-butene-1,4-diamine; tetrakis(dimethylamino)-ethylene; 2,2'-oxybis (ethylamine); 4,9-dioxa-1,12-dodecanediarmine; 4,7,10-trioxa-1, 13-tridecanediamine; 1,3-diamino-2-hydroxypropane; 2-(2-aminoethylamino)ethanol;1,3-bis (dimethylamino)-2-propanol; n,n'-bis(2-hydroxyethyl) ethylenediamine; n,n,n,'n'-tetrakis(2-hydroxy-propyl) ethylenediamine; pentrol; 2-(aminomethyl)-1-ethylpyrrolidine; 2-(2-aminoethyl)-1-methylpyrrolidine, (S)-(+)-1,(2-pyrrolidinylmethyl)pyrrolidine; dipiperidinomethane; 1,1'-methylenebis(3-methylpiperidine); 4-piperidinopiperidine; 4,4'-ethylenedipiperidine 4,4'-trimethylenedipiperidine; 4,4'-trimethylenebis(1-methylpiperidine); 4,4'-trimethylenebis(1-piperidineethanol); 1-(2-aminoethyl)-piperidine; 1-(3-aminopropyl)-2-pipecoline; 1-methyl-4-(methylamino) piperidine; 4-(aminomethyl) piperidine; 4-amino-2,2,6,6-tetramethylpiperidine; 4-dimethylamino-2-2,6,6-tetramethylpiperidine; 2-methyl-2-imidazoline; 4,4-dimethyl-2-imidazoline; 2-methylthio-2-imidazoline; piperazine; 1-methylpiperazine; 1,4-dimethylpiperazine; 2-methylpiperazine; 2,6-dimethylpiperazine; trans-2,5-dimethylpiperazine; 4-(dimethylamino)-1,2,2,6,6-pentamethylpiperidine; 1-(3-chloropropyl)piperazine; 1-(2-hydroxyethyl)piperazine; 1,4-bis(2-hydroxyethyl) piperazine; 1-(2-(2-hydroxyethoxy)ethyl) piperazine; 1-amino-4-methylpiperazine; 1-amino-4-(2-hydroxyethyl) piperazine; 1-(2aminoethyl)piperazine; 1,4-bis(3-aminopropyl)-piperazine hexetidine; mixture of stereoisomers, 1,4,5,6-tetrahydropyrimidine; homopiperazine; 1,3,5-trimethylhexahydro-1,3,5-trizaine; 1,3,5-triethylhexahydro-1,3,5-triazine; 1,4,7-triazacyclononane; 1,4,7-trimethyl-1,4,7-trizacyclononane; 1,5,9-triazacyclododecane; 1,5,9-trimethyl-1,5,9-triazacyclodododecane; cyclen; 1,4,8,11-tetraazacyclotetradecane; 1,4,8,11-tetramethyl-1,4,11-tetraazacyclotetradecane; 1,4,8,12-tetraazacyclopentadecane; hexacyclen tri sulfate; 1,4,7,10, 13,16-hexamethyl-1,4,7,10,13,16-hexaazacyclooctadecane; 1,4-diazabicyclo(2.2.2)octane; Dabco 33-LV; (−)sparteine sulfate pentahydrate; 1,3,4,6,7, 8-hexahydro-2h-pyrimido(1,2-a)pyrimidine; 1,3,4,6,7,8-hexahydro-1-methyl-2H-pyrmidido( 1,2-A)-pyrimidine; hexamethylenetetramine; 4-(2-arninoethyl)morpholine; 4-(2-dimethylamino)ethyl)morpholine; 1,4,10,13-tetraoxa-7,16-diazacyclooctadecane, 4,7,13,18-tetraoxa-1,10-diazabicyclo(8,5,5)eicosane; 4,7,13,16,21,22-pentaoxa-1,10-diazabicyclo(8,8,5)-tricosane; and 4,7,13,16,21,24-hexaoxa-1,10-diazabicyclo(8,8,8)-hexacosane.

Having now generally described this invention, the same will become better understood by reference to certain specific examples which are included herein for purposes of illustration only and are not intended to be limiting unless otherwise specified. All US patents and patent applications cited herein are fuilly incorporated by reference.

EXAMPLES

Experimental Apparatus and Conditions for Examples

Capillary electrophoretic separations were performed with a Waters Quanta® 4000E CE unit, Waters Corporation, Milford, Mass. Separations were performed in fused silica capillaries, the dimensions specified in the specific examples. Likewise, the magnitude of the voltages are also described in the specific examples. Injection was achieved by raising the inlet end of the capillary immersed in the sample solution to a height of 10 cm above the outlet end for either 2 or 5 seconds. On-column UV detection was performed at 214 nm. Data collection was achieved with Waters Millennium® software v.2. 1(Waters Corporation, Milford, Mass.).

Example 1

Figure 2A:
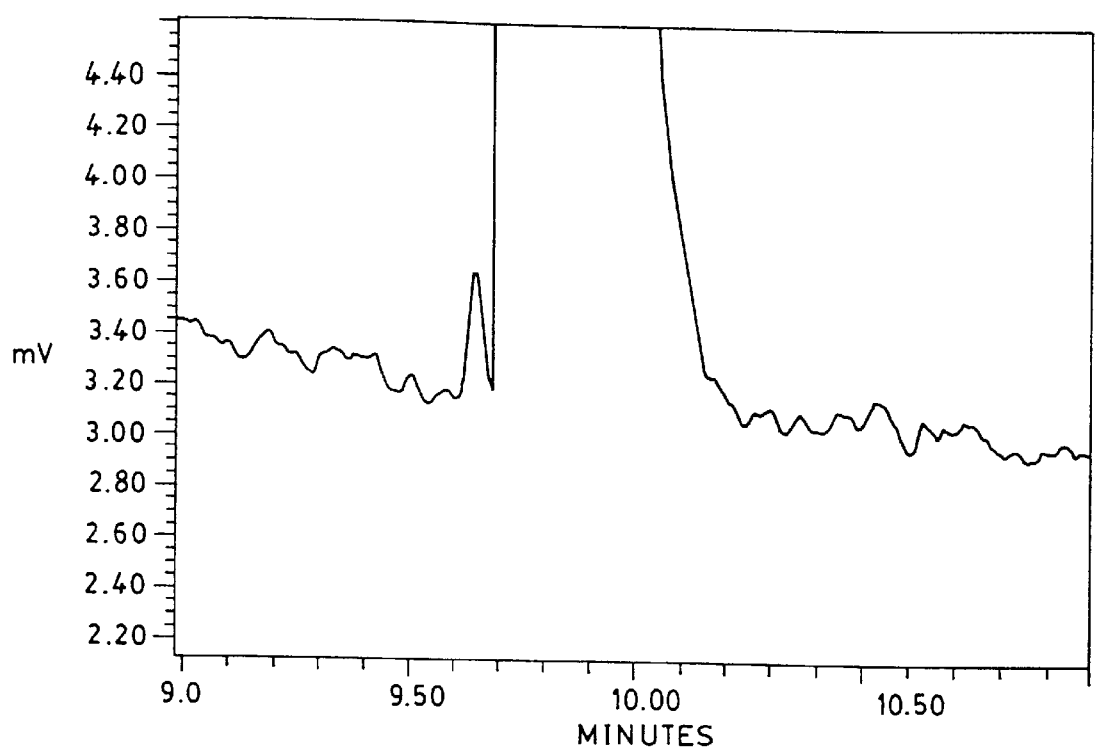
Figure 2B:
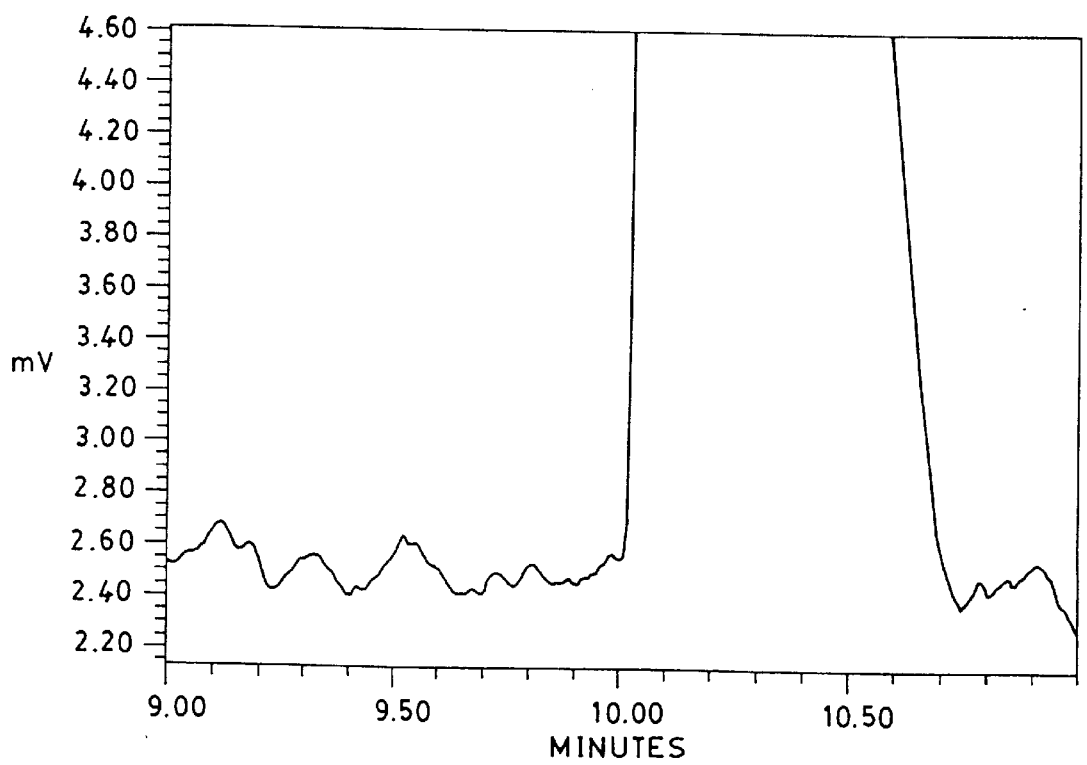

Separation of 99% (+) and 1% (−) Ephedrines in Normal Buffer, 2-Second Injection FIG. 2 shows the separation of 1% (−)-ephedrine in the presence of (+)-ephedrine with 25 mM (S)-N-dodecoxycarbonylvaline and common MEKC buffering agents, 25 mM $Na_2HPO_4$/25 mM $Na_2B_4O_7$. The pH of 25 mM $Na_2HPO_4$/25 mM $Na_2B_4O_7$ is 9.5 in the absence of the surfactant. However, because the surfactant is in the protonated form, when it is dissolved in the electrolyte, the pH drops to 8.8. The electrolyte pH is then adjusted to 8.5 with 1.4 M phosphoric acid. The separation was performed in a 60 cm×100 µm i.d. capillary with a voltage of +15,000 volts. The current was 275 µA. The sample was 0.01 mg/mL (−)-ephedrine and 0.99 mg/mL (+)-ephedrine in water.

In the top separation, a hydrostatic injection time of 2 seconds was employed. The resolution was 1.3. The signal for the minor peak was 0.5 mAU, while the noise, measured as peak-to-peak from 9.0 to 9.5 minutes, was 0.25 mAU. Therefore, the S/N was 2, which is generally defined as the detection limit.

Example 2

Separation of 99% (+) and 1% (−) Ephedrines in Normal Buffer, 5-Second Injection To increase detectability, a 5 second hydrostatic injection time was employed. This separation is shown in the bottom of FIG. 2. Expectedly, resolution was not achieved at this higher sample load.

The poor resolution and high background noise (0.25 mAU) for both examples 1 and 2 with the surfactant/phosphate/borate combination is due to the fact that the power generated under these experimental conditions was 6.9 W/m. It has been recommended that power levels be kept below 1 W/m to minimize band broadening due to Joule heating (Sepaniak, M. J. and Cole, R. O. Analytical Chemistry, 1987, (59) 472–477). Therefore, a power level of 6.9 W/m would be expected to decrease resolution. Furthermore, with forced air convection and a power level of 6.9 W/m, the temperature inside the capillary has been calculated to be 35° C. above the temperature outside the capillary (25° C. in this case) (Nelson, R. J. et al. supra). At a temperature of 60° C., the electrolyte may outgas, evaporate, and/or degrade, which would explain the high noise level. Furthermore, reproducibility would suffer due to electrolyte evaporation and degradation.

Example 3

Figure 3A:
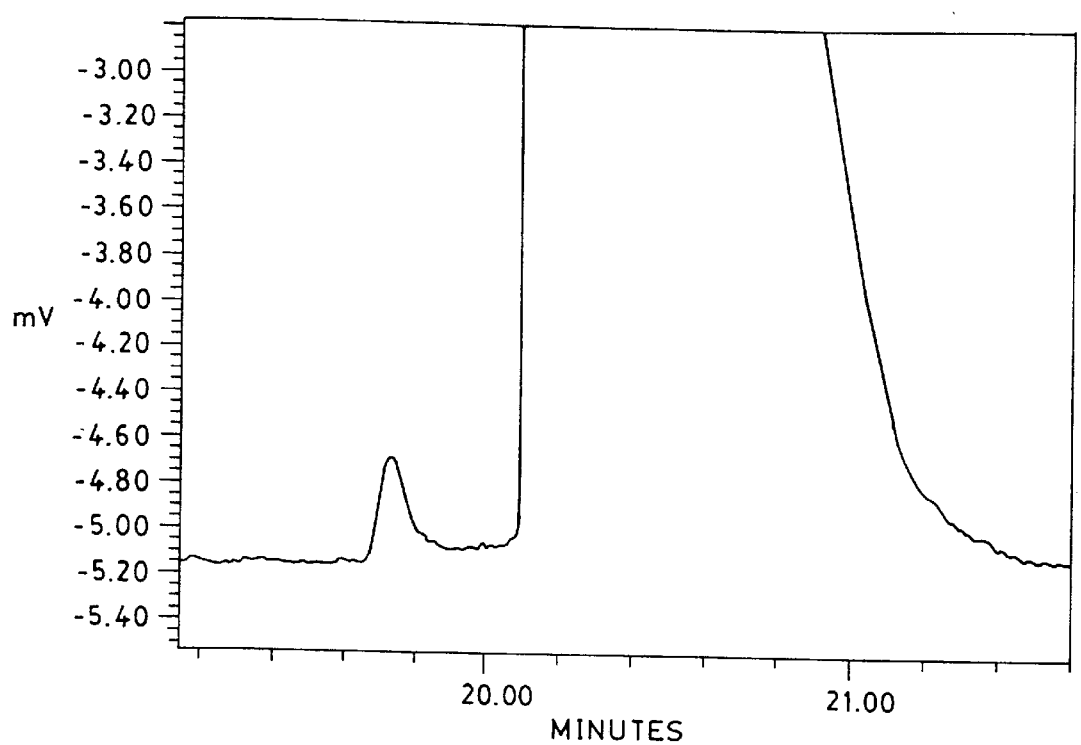
Figure 3B:
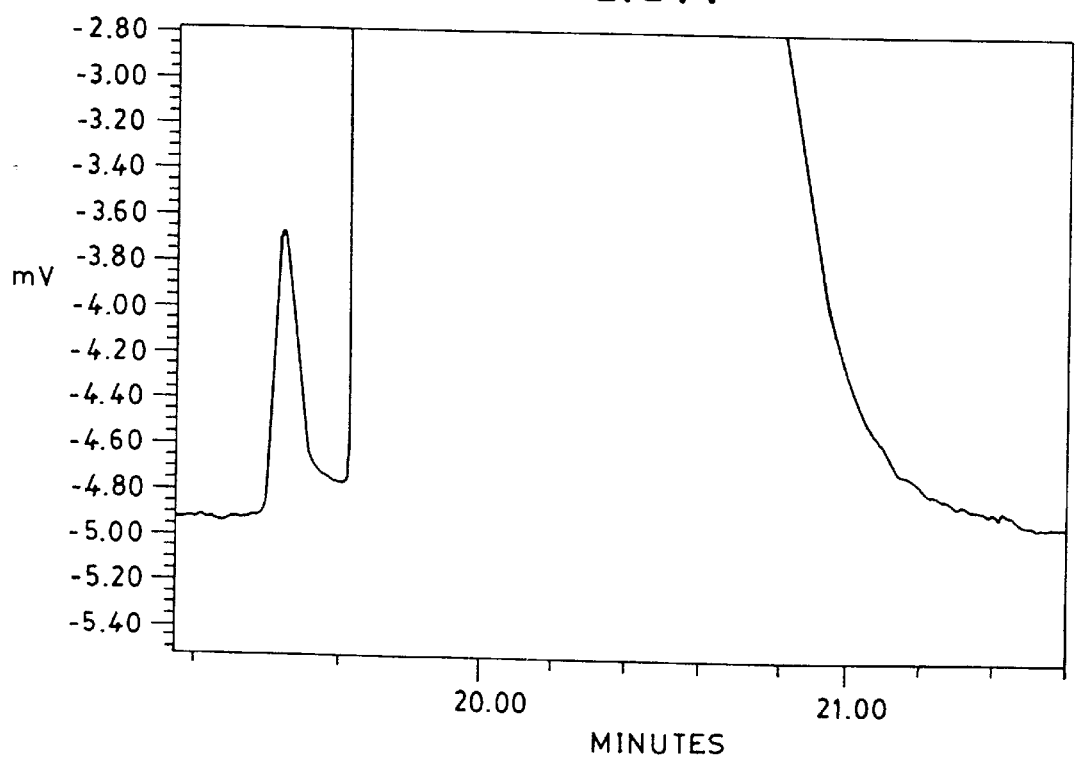

Separation of 99% (+) and 1% (−) Ephedrines with Bis-tris Propane Buffer, 2-Second Injection FIG. 3 shows the separation of 1% (−)-ephedrine in the presence of (+)-ephedrine with 25 mM (S)-N-dodecoxycarbonylvaline and 50 mM bis-tris propane (see FIG. 5), a biological buffer available from Aldrich Chemical Co. Inc., 1001 W. St. Paul Ave., Milwaukee, Wis. 53233. In the absence of surfactant, the pH of 50 mM bis-tris propane is 10.6. When the electrolyte is made 25 mM in the surfactant, the pH drops to 9.3. The electrolyte pH was then adjusted to 8.5 with 1.4 M phosphoric acid. The separation was performed in a 60 cm×100 µm i.d. capillary with a voltage of +15,000 volts. The current was 35 µA.

The top separation in FIG. 3 employed a 2 second hydrostatic injection. The resolution was 3.5. The signal for the minor peak was 0.5 mAU, while the noise, measured as peak-to-peak from 19.0 to 19.5 minutes, was 0.07 mAU. The S/N was 7.1, 3× the S/N obtained with the phosphate/borate buffer (FIG. 2, top separation). The improved S/N is due to the decreased noise with the bis-tris propane buffer (0.07 mAu vs. 0.25 mAU). The power level with the bis-tris propane buffer was 0.9 W/m, below the recommended maximum of 1 W/m. Furthermore, the temperature rise above ambient was calculated to be 4.5° C. at a power level of 0.9 W/m with forced air convection (Nelson, R. J. supra). The lower power level affords higher resolution and better detectability.

Example 4

Separation of 99% (+) and 1% (−) Ephedrines in Bis-tris Propane Buffer, 5-Second Injection The bottom separation in FIG. 3 employed a 5 second hydrostatic injection. Note that sufficient resolution (Rs=1.4) is maintained while the S/N increases to 18.6. The higher resolution obtained with the surfactant/bis-tris propane combination allows more sample to be injected for better detectability while still maintaining sufficient resolution.

Example 5

Figure 4:
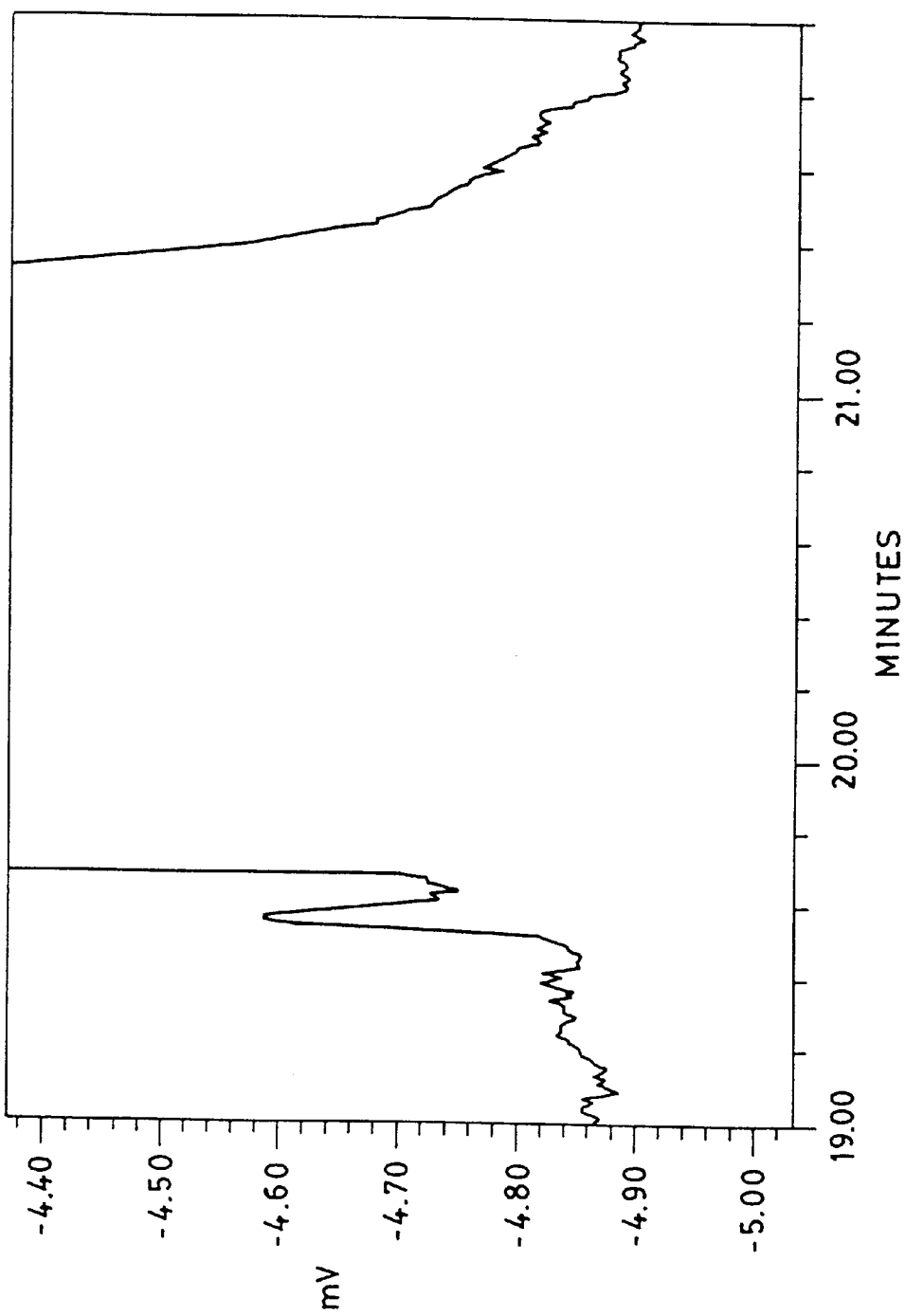
FIG. 4 is a chromatogram showing the separation of 0.1% (−)-ephedrine in the presence of (+)-ephedrine using 25 mM (S)-N-dodecoxycarbonylvaline and 50 mM bis-tris propane, pH 8.5, in a 100 μm i.d. capillary.

Separation of 99.9% (+) and 0.1% (−) Ephedrines in Bis-tris Propane Buffer, 5-Second Injection This point is further illustrated in FIG. 4, where a 0.1% level of (−)-ephedrine can be detected with a 5 second hydrostatic injection. In this case, the S/N was 2.2. Due to a lower noise level and higher resolution, the surfactant/bis-tris propane combination offers an order of magnitude decrease in detection limit compared to the one buffered with an equivalent concentration of phosphate/borate (0.1% vs. 1.0%).

Examples 6–7

Separation of Racemic (+/−) Norephedrines in Both Buffers.

FIGS. 6A and 6B show the separation of norephedrine enantiomers using 25 mM (S)-N-dodecoxycarbonylvaline and 25 mM $Na_2HPO_4$/25 mM $Na_2B_4O_7$ (FIG. 6A), and the identical separation using 50 mM bis-tris propane buffer (FIG. 6B), both at pH 8.5. The voltage was 15 kV, the capillary 50 µm i.d.×60 cm, the hydrostatic injection time 2 seconds, and the sample 0.4 mg/mL racemic norephedrine dissolved in electrolyte.

With phosphate/borate (FIG. 6A), the current was 45 µA, resulting in a power level of 1.1 W/m. The resolution was 3.0 and the electroosmotic mobility was $5.7 \times 10^{-4}$ $cm^2$/Vs. With bis-tris propane (FIG. 6B), the current was 10.5 µA, resulting in a power level of 0.3 W/m. The resolution was 3.9 and the electroosmotic mobility was $3.6 \times 10^{-4}$ $cm^2$/Vs. Higher resolution was obtained with the surfactant/bis-tris propane combination due to the lower electroosmotic flow. Furthermore, because the conductivity of the surfactant/bis-tris propane combination is low, the voltage can be increased to 30 kV with the wattage only increasing to 1.1 W/m (22 µA). Analysis time is decreased from 19.8 minutes to 9.1 minutes, while the resolution actually increases to 4.0 (FIG. 7). When the voltage is increased to 30 kV with the surfactant/phosphate/borate combination, the wattage increases to 7.1 W/m (142 µA) and the resolution decreases to 2.0.

Table 1 summarizes the data generated from the above examples.

TABLE 1

Separation of Ephedrine Enantiomers Using Two Surfactant/Buffer Combinations

| Buffer Type | Buffer Conc. (mM) | Surfactant Conc. (mM) | Injection Time (Sec) | Ephedrine Ratio (+/−) | Power Level (W/m) | S/N (Minor Peak) | Resolution |
|---|---|---|---|---|---|---|---|
| Phosphate/Borate | 50 | 25 | 2 | 99/1 | 6.9 | 2 | 1.3 |
| Phosphate/Borate | 50 | 25 | 5 | 99/1 | 6.9 | — | 0 |
| Bis-Tris Propane | 50 | 25 | 2 | 99/1 | 0.9 | 7.1 | 3.5 |
| Bis-Tris Propane | 50 | 25 | 5 | 99/1 | 0.9 | 18.6 | 1.4 |
| Bis-Tris Propane | 50 | 25 | 5 | 99.9/0.1 | 0.9 | 2.2 | 1.4 |

The detection limit is a full order of magnitude lower for the invention (see last row, S/N 2.2 for 0.1% ephedrine in bis-tris propane buffer, vs. top row, S/N 2.0 for 1% ephedrine in phosphate/borate buffer) than for the present state-of-the-art.

Example 8

(S)-N-Dodecoxycarbonylvaline with N,N'-bis(2-Aminoethyl)-1,3-Propanediamine

The electrolyte contained 25 mM (S)-N-dodecoxycarbonylvaline and 25 mM N,N'-bis(2-aminoethyl)-1,3-propanediamine, pH 9.6 (unadjusted). The capillary was 75 μm i.d.×35 cm length. With an applied voltage of +20 kV, the current was 27 μA, for a power level of 2 W/m. The electroosmotic flow was $1.9 \times 10^{-4}$ cm$^2$/Vs, a three to four-fold reduction in the normal EOF at this pH. These conditions permitted the baseline separation of metoprolol enantiomers in 7 minutes, FIG. 9.

Example 9

(S)-N-Dodecoxycarbonylvaline with Pentrol

The electrolyte contained 25 mM (S)-N-dodecoxycarbonylvaline and 50 mM pentrol, pH 8.0 with phosphoric acid. The capillary was 75 μm i.d.×60 cm length. With an applied voltage of +30 kV, the current was 25 μA, for a power level of 1.25 W/m. The electroosmotic flow was $2.1 \times 10^{-4}$ cm$^2$/Vs, a three to four-fold reduction in the normal EOF at this pH. These conditions permitted the baseline separation of benzoin enantiomers, FIG. 10.

Example 10

(S)-N-Dodecoxycarbonylvaline with Pentaethylenhexamine

The electrolyte contained 25 mM (S)-N-dodecoxycarbonylvaline and 15 mM pentaethylenehexarnine, pH 9.6 (unadjusted). The capillary was 75 μm i.d.×60 cm length. With an applied voltage of +30 kV, the current was 6 μA, for a power level of 0.3 W/m. The electroosmotic flow was $3.8 \times 10^{-4}$ cm$^2$/Vs, a two-fold reduction in the normal EOF at this pH. Note that this reduction was achieved with only 15 mM of this hexaaamine, and that the current generated was extremely low. These conditions permitted the baseline separation of norphenylephrine enantiomers in 6 minutes, FIG. 11.

Example 11

(S)-N-Dodecoxycarbonylvaline with 4,7,10-Trioxa-1,13-Tridecanediamine

The electrolyte contained 25 mM (S)-N-dodecoxycarbonylvaline and 20 mM 4,7,10-trioxa-1,13-tridecanediamine, pH 9.5 (unadjusted). The capillary was 75 μm i.d.×60 cm length. With an applied voltage of +30 kV, the current was 10 μA, for a power level of 0.5 W/m. The electroosmotic flow was $3.4 \times 10^{-4}$ cm$^2$/Vs, a two-fold reduction in the normal EOF at this pH. Note that this reduction was achieved with only 20 mM of this diamine, and that the current generated was extremely low. These conditions permitted the baseline separation of metoprolol enantiomers, FIG. 12.

Example 12

Carboxymethyl-β-Cyclodextrin with Bis-tris Propane vs. Sodium Tetraborate

The top separation (FIG. 14A) was obtained using an electrolyte containing 0.1% (w/v) carboxymethyl-β-cyclodextrin and 25 mM bis-tris propane, pH adjusted to 8.5 with phosphoric acid. The capillary was 75 μm i.d.×60 cm length. With an applied voltage of +25 kV, the current was 25 μA, for a power level of 1.0 W/m. The electroosmotic flow was $4.4 \times 10^{-4}$ cm$^2$/Vs. The enantiomers of verapamil were separated with a resolution of 1.6. The bottom separation (FIG. 14B) was obtained using an electrolyte containing 0.1% (w/v) carboxymethyl-β-cyclodextrin and 25 mM sodium tetraborate, pH adjusted to 8.5 with phosphoric acid. The capillary was 75 μm i.d.×60 cm length. With an applied voltage of +25 kV, the current was 140 μA for a power level of 5.8 W/m. The electroosmotic flow was $8.2 \times 10^{-4}$ cm$^2$/Vs. The enantiomers of verapamil were separated with a resolution of only 0.2, and were not fully resolved from the EOF marker. Therefore, the electrolyte containing bis-tris propane offered an increase in resolution by a factor of eight (due to lower EOF and wattage) while decreasing the power level six-fold.

Example 13

Succinylated-β-Cyclodextrin with Bis-tris Propane vs. Sodium Tetraborate

The top separation (FIG. 15A) was obtained using an electrolyte containing 0.1% (w/v) succinylated-β- cyclodextrin and 25 mM bis-tris propane, pH adjusted to 8.5 with phosphoric acid. The capillary was 75 βm i.d.×60 cm length. With an applied voltage of +30 kV, the current was 20 μA, for a power level of 1.0 W/m. The electroosmotic flow was $4.4 \times 10^{-4}$ cm$^2$/Vs. The enantiomers of verapamil were separated with a resolution of 3.0. The bottom separation (FIG. 15B) was obtained using an electrolyte containing 0.1% (w/v) succinylated-β-cyclodextrin and 25 mM sodium tetraborate, pH adjusted to 8.5 with phosphoric acid. The capillary was 75 μm i.d.×60 cm length. With an applied voltage of +30 kV, the current was 195 μA, for a power level of 9.8 W/m. The electroosmotic flow was $8.3 \times 10^{-4}$ cm$^2$/Vs. The enantiomers of verapamil were separated with a resolution of only 0.4. Therefore, the electrolyte containing bis-tris propane offered an increase in resolution by a factor of seven (due to lower EOF and wattage) while decreasing the power level ten-fold.

Example 14

18-Crown-6-Tetracarboxylic Acid with Bis-tris Propane vs. Sodium Tetraborate

The top separation (FIG. 16A) was obtained using an electrolyte containing 5 mM 18-crown-6-tetracarboxylic acid and 25 mM bis-tris propane, pH adjusted to 8.5 with phosphoric acid. The capillary was 75 μm i.d.×60 cm length. With an applied voltage of +25 kV, the current was 26 μA, for a power level of 1.1 W/m. The electroosmotic flow was $4.2 \times 10^{-4}$ cm$^2$/Vs. The enantiomers of methylbenzylamine were separated with a resolution of 1.5. The bottom separation (FIG. 16B) was obtained using an electrolyte containing 5 mM 18-crown-6-tetracarboxylic acid and 25 mM sodium tetraborate, pH adjusted to 8.5 with phosphoric acid. The capillary was 75 μm i.d.×60 cm length. With an applied voltage of +25 kV, the current was 120 μA, for a power level of 5.0 W/m. The electroosmotic flow was $8.4 \times 10^{-4}$ cm$^2$/Vs. The enantiomers of methylbenzylamine were not separated at all. Therefore, the electrolyte containing bis-tris propane offered baseline resolution compared to none (due to lower EOF and wattage) while decreasing the power level five-fold.

Example 15

Lauric Acid with Bis-tris Propane vs. Sodium Phosphate/sodium Tetraborate

FIG. 17 shows the baseline separation of the diastereomers of nadolol using an electrolyte containing 25 mM lauric acid and 50 mM bis-tris propane, pH adjusted to 8.5 with phosphoric acid. The capillary was 75 μm i.d.×60 cm length. With an applied voltage of +25 kV, the current was 25 μA, for a power level of 1.0 W/m. The electroosmotic mobility was $3.8 \times 10^{-4}$ cm$^2$/Vs. FIG. 18 shows no separation for the diastereomers of nadolol, and was obtained with an electrolyte containing 25 mM lauric acid, 25 mM disodium phosphate/25 mM sodium tetraborate, pH 8.5 with phosphoric acid. With an applied voltage of +25 kV, the current was 270 μA, for a power level of 11 W/m. The electroosmotic mobility was $5.9 \times 10^{-4}$ cm$^2$/Vs. In this example, bis-tris propane afford baseline resolution vs. zero resolution, and an 11-fold reduction in power level. Furthermore, S/N is improved due to lower noise and increased signal due to sharper peaks.

Example 16

Protonated Dodecylsulfate with Bis-tris Propane vs. Sodium Dodecylsulfate with Sodium Phosphate/sodium Tetraborate FIG. 19 shows the separation of eleven priority pollutant phenols using an electrolyte containing 43 mM protonated dodecylsulfate and 43 mM bis-tris propane, pH 8.6 (unadjusted). Eleven peaks can be distinguished, with all baseline resolved except the pair at 15.5 minutes. The capillary was 75 μm i.d.×60 cm length. With an applied voltage of +25 kV, the current was 24 μA, for a power level of 1.0 W/m. The electroosmotic mobility was $4.4 \times 10^{-4}$ cm$^2$/Vs. FIG. 20 shows the separation of the same sample using an electrolyte containing 43 mM sodium dodecylsulfate and 21.5 mM disodium phosphate/21.5 mM sodium tetraborate, pH adjusted to 8.6 with phosphoric acid. Only eight peaks can be distinguished. The capillary was 75 μm i.d.×60 cm length. With an applied voltage of +25 kV, the current was 200 μA, for a power level of 8.0 W/m. The electroosmotic mobility was $7.3 \times 10^{-4}$ cm$^2$/Vs. In this example, the protonated version of dodecylsulfate in combination with bis-tris propane offered improved resolution (due to lower EOF and lower wattage) and an eight-fold reduction in the power level.

TABLE 2

Summary of Different Additives with Bis-Tris Propane vs. Inorganic Buffers

| Additive | Bis-Tris Propane | | | Inorganic Buffer | | |
|---|---|---|---|---|---|---|
| | EOF[1] | Rs | Power[2] | EOF[1] | Rs | Power[2] |
| carboxymethyl-β-CD | 4.4 | 1.6 | 1.0 | 8.2 | 0.2 | 5.8 |
| succinylated-β-CD | 4.4 | 3.0 | 1.0 | 8.3 | 0.4 | 9.8 |
| 18-crown-6-tetracarboxylic acid | 4.2 | 1.5 | 1.1 | 8.4 | 0 | 5.0 |
| lauric acid | 3.8 | 1.5 | 1.0 | 5.9 | 0 | 11 |
| dodecylsulfate | 4.4 | 11 peaks | 1.0 | 7.3 | 8 peaks | 8.0 |

[1]- units of $10^{-4}$ cm$^2$/Vs
[2]- units of Watts/m

Example 17

Tetradecytrimethylammonium Hydroxide with Citric Acid vs Phosphate

FIG. 21 shows the separation of CBZ-valine and CBZ-norvaline (0.2 mg/mL each in electrolyte) with 20 mM tetradecyltrimethylammonium hydroxide as the EKC additive and a common MEKC buffering agent, 25 mM NaH$_2$PO$_4$. The pH of 25 mM NaH$_2$PO$_4$ is 4.5. However, because the surfactant is in the hydroxide form, when it is dissolved in the electrolyte, the pH drops to 8. The electrolyte pH is then adjusted to 3.0 with 1.4 M phosphoric acid. Injection was performed by raising the inlet 10 cm higher than the outlet for 5 seconds. The separation was performed in a 60 cm×75 μm i.d. capillary with a voltage of −30,000 volts. The current was 84 μA, generating a power level of 4.2 W/m. The electroosmotic flow rate was $-8.4 \times 10^{-4}$ cm$^2$/Vs. As seen in FIG. 21, no separation was obtained.

The poor resolution with the surfactant/phosphate combination is due to the fact that the power generated under these experimental conditions was 4.2 W/m and because the EOF was rather fast. It has been recommended that power levels be kept below 1 W/m to minimize band broadening due to Joule heating (Sepaniak, M. J. and Cole, R. O. Analytical Chemistry, 1987, (59) 472–477). Therefore, a power level of 4.2 W/m would be expected to decrease resolution. The fast EOF leads to a small migration window, decreasing resolution.

FIG. 22 shows the separation of CBZ-valine and CBZ-norvaline (0.2 mg/mL each in electrolyte) with 20 mM tetradecyltrimethylammonium hydroxide as the EKC additive and 25 mM citric acid as the buffer. The natural pH of this electrolyte is 3.0, a pH at which citrate anion has excellent buffering capacity. Injection was performed by raising the inlet 10 cm higher than the outlet for 5 seconds. The separation was performed in a 60 cm×75 µm i.d. capillary with a voltage of −30,000 volts. The current was 16 µA, generating a power level of 0.8 W/m. The electroosmotic flow rate was −4.7×10$^{-4}$ cm$^2$/Vs. As seen in FIG. 22, the two analytes are baseline resolved.

Baseline resolution is obtained with the citrate-containing electrolyte because the EOF is decreased by a factor of two compared to the phosphate electrolyte, and because the power level is reduced by a factor of five. It is surprising that the EOF would be reduced with this electrolyte while the power was also reduced. The reduced EOF can be explained by the fact that citrate is a polycarboxylic acid that can bind strongly to the positively charged wall, reducing EOF.

When 1 mg/mL CBZ-norvaline is separated with the citrate electrolyte and a 20 second injection, it is found to be contaminated with 1% CBZ-valine, FIG. 23.

Example 18

Calculated Conductivities for Reagents of Examples 1–17

The conductivities of reagents of example 1–17 were calculated and are set forth in table 3. The actual measured conductivities correspond closely with the calculated values set forth in table 3.

TABLE 3

Calculated Conductivities for Patent Examples Using Conductivity Equation

| Patent Example | Additive | Additive Conc. (mM) | Buffer Composition | Buffer Conc. (mM) | Adjusted Final pH | Capillary ID (µm) | Capillary Length (cm) | CE Voltage Length Volts | CE Current µ Amperes | Conductivity Equation k = I*L/V*A (mS/cm) |
|---|---|---|---|---|---|---|---|---|---|---|
| 1 | (S)-N-Dodecoxycarbonylvaline | 25 | Phosphate/Borate | 25/25 | 8.5 | 100 | 60 | 15000 | 275 | 14.013 |
| 2 | (S)-N-Dodecoxycarbonylvaline | 25 | Phosphate/Borste | 25/25 | 8.5 | 100 | 60 | 15000 | 275 | 14.013 |
| 3 | (S)-N-Dodecoxycarbonylvaline | 25 | Bis-Tris propane | 50 | 8.5 | 100 | 60 | 15000 | 35 | 1.783 |
| 6 | (S)-N-Dodecoxycarbonylvaline | 25 | Phosphate/Borate | 25/25 | 8.5 | 50 | 60 | 15000 | 45 | 9.172 |
| 7 | (S)-N-Dodecoxycarbonylvaline | 25 | Bis-Tris propane | 50 | 8.5 | 50 | 60 | 15000 | 10.5 | 2.140 |
| 6a | (S)-N-Dodecoxycarbonylvaline | 25 | Phosphate/Borate | 25/25 | 8.5 | 50 | 60 | 30000 | 142 | 14.471 |
| 7a | (S)-N-Dodecoxycarbonylvaline | 25 | Bis-Tris propane | 50 | 8.5 | 50 | 60 | 30000 | 22 | 2.242 |
| 8 | (S)-N-Dodecoxycarbonylvaline | 25 | N,N-bis(2-aminoethyl)-1,3-propanediamine | 25 | 9.6 | 75 | 35 | 20000 | 27 | 1.070 |
| 9 | (S)-N-Dodecoxycarbonylvaline | 25 | pentrol | 50 | 8.0 | 75 | 60 | 30000 | 25 | 1.132 |
| 10 | (S)-N-Dodecoxycarbonylvaline | 25 | pentaethylenehexamine | 15 | 9.6 | 75 | 60 | 30000 | 6 | 0.272 |
| 11 | (S)-N-Dodecoxycarbonylvaline | 25 | 4,7,10-trioxa-1,13-tridecanediamine | 20 | 9.5 | 75 | 60 | 30000 | 10 | 0.453 |
| 12a | cycrodextrin | 0.1% w/v | Bis-Tris propane | 25 | 8.5 | 75 | 60 | 25000 | 25 | 1.359 |
| 12b | cyclodextrin | 0.1% w/v | Sodium TetraBorate | 25 | 8.5 | 75 | 60 | 25000 | 140 | 7.609 |
| 13a | cyclodexirin | 0.1% w/v | Bis-Tris propane | 25 | 8.5 | 75 | 60 | 30000 | 20 | 0.906 |
| 13b | cyclodextrin | 0.1% w/v | Sodium TetraBorate | 25 | 8.5 | 75 | 60 | 30000 | 195 | 8.832 |
| 14a | 18-crown-6 | 5 | Bis-Tris propane | 25 | 8.5 | 75 | 60 | 25000 | 26 | 1.413 |
| 14b | 18-crown-6 | 5 | Sodium TetraBorate | 25 | 8.5 | 75 | 60 | 25000 | 120 | 6.522 |
| 15a | Lauric Acid | 25 | Bis-Tris propane | 50 | 8.5 | 75 | 60 | 25000 | 25 | 1.359 |
| 15b | Lauric Acid | 25 | Phosphate/Borate | 25/25 | 8.5 | 75 | 60 | 25000 | 270 | 14.675 |
| 16a | Protonated Dodecyl Sulfate | 43 | Bis-Tris propane | 43 | 8.6 | 75 | 60 | 25000 | 24 | 1.304 |
| 16b | Sodium Dodecyl Sulfate | 43 | Phosphata/Borate | 21.5/21.5 | 8.6 | 75 | 60 | 25000 | 200 | 10.870 |
| 17 | Tetradecyl-trimethyl-ammonium Hydroxide | 20 | Phosphate | 25 | 3.0 | 75 | 60 | 30000 | 84 | 3.805 |
| 17 | Tetradecyl-trimethyl-ammonium Hydroxide | 20 | citric acid | 25 | 3.0 | 75 | 60 | 30000 | 16 | 0.725 |

We claim:

1. A capillary electrophoresis reagent for isolating one or more analytes contained in a sample, comprising: an aqueous phase for receiving said sample and forming a solution of said analyte, said aqueous phase having a partitioning additive and buffering means, said partitioning additive selected from the group consisting of cyclodextrins, polymer ions, proteins and surface active agents, said partitioning additive in an amount to allow partitioning of analyte from solution to the partitioning additive; said buffering means comprising a polyamine for partitioning additives which are neutral to acidic and a polycarboxylate for partitioning additives which are neutral to basic, said buffering means at a concentration to maintain a pH of 2–7 when said aqueous phase is neutral to acidic and a pH of 7–12 when said aqueous phase is neutral to basic, said aqueous phase with said partitioning additive and buffering means having a conductivity of 0.5 to 2.0 mS/cm.

2. The reagent of claim 1 wherein said partitioning additive is a surface active agent, said surface active agent in said aqueous phase at a concentration sufficient to form one or more micelles, said surface active agent comprising an anionic surfactant for aqueous phases which are neutral to basic, and said surface active agent comprising a cationic surfactant for aqueous phases which are neutral to acidic.

3. The reagent of claim 2 wherein said anionic surfactant is selected from the group consisting of fatty acids having chain lengths of 8 to 20 carbons, long chain sulfonates, and alkyl aryl sulfonates.

4. The reagent of claim 2 wherein said anionic surfactant is selected from the group of chiral surfactants consisting of (S)-N-dodecoxycarbonylvaline, (S)-2-[(1-oxododecoxy)amino)]-3-methyl-1-sulfooxybutane, (R)-N-dodecoxycarbonylvaline, (S)-N-dodecoxycarbonyl-tert-leucine, (S)-N-tetradecoxycarbonylvaline, (S)-N-dodecoxycarbonylphenylglycine, (S)-N-dodecoxycarbonylserine, (S)-N-dodecoxycarbonylalanine, (S)-N-dodecoxycarbonylleucine, and (S)-N-dodecoxycarbonylproline.

5. The reagent of claim 2 wherein said cationic surfactant is selected from the group of surfactants consisting of long-chain amines and quaternary ammonium salts.

6. The reagent of claim 2 wherein said cationic surfactant is selected from the group consisting of tetradecyltrimethylammonium, cetylpyridinium, dodecyltrimethylammonium, and hexadecyltrimethylammonium.

7. The reagent of claim 1 wherein said polyamine, has the following structural formula:

R'—NH—[CH$_2$]$_a$—NH—R wherein a is a numeral from about 1 to 8; and

R and R' are the same or different and may be alkyl, alkenyl or alkynyl substituents, branched or straight chain, substituted or unsubstituted, having from about 1 to 8 carbons, and may have one or more hydrophilic moities such as hydroxy, sulfhydryl, or amine.

8. The reagent of claim 1 wherein said polyamine is bis-tris propane.

9. The reagent of claim 1 wherein said partitioning additive is selected from the group consisting of carboxymethyl-β-cyclodextrin, succinylated-β-cyclodextrin, protonated crown ether acid derivatives, and 18-crown-6-tetracarboxylic acid.

10. The reagent of claim 1 wherein said polycarboxylate is selected from the group consisting of succinnic acid, citric acid, cis-aconitic acid, iso-citric acid, glutaric acid, fumaric acid, malic acid, and oxaloacetic acid.

11. A kit for forming a electrokinetic reagent comprising a container having means for forming a aqueous phase having one or more analytes in solution, said means comprising a partitioning additive and a buffering means, said partitioning additive selected from the group consisting of cyclodextrins, polymer ions, proteins and surface active agents, said partitioning additive in an amount to allow partitioning of analytes from solution to the partitioning additive; said buffering means is present in said aqueous phase at a concentration to maintain the pH of said aqueous phase at pH of 2–7 for neutral to acidic aqueous phases and a pH of 7–12 for neutral to basic aqueous phases, said buffering means comprising a polyamine for partitioning additives which are neutral to acidic and a polycarboxylate for partitioning additives which are neutral to basic, said aqueous phase with said surface active reagent and buffering means having a conductivity of 0.5 to 2.0 mS/cm.

12. The kit of claim 11 wherein said partitioning additive is a surface active agent, said surface active agent is present in said aqueous phase at a concentration to form one or more micelles, said surface active agent comprising an anionic surfactant for aqueous phases which are neutral to basic, and said surface active agent comprising a cationic surfactant for aqueous phases which are neutral to acidic.

13. The reagent of claim 12 wherein said anionic surfactant is selected from the group comprising fatty acids having chain lengths of 8 to 20 carbons, long chain sulfonates, and alkyl aryl sulfonates.

14. The kit of claim 12 wherein said anionic surfactant is selected from the group of chiral surfactants consisting of (S)-N-dodecoxycarbonylvaline, (S)-2-[(1-oxododecoxy)amino]-3-methyl-1-sulfooxybutane, (R)-N-dodecoxycarbonylvaline, (S)-N-dodecoxycarbonyl-tert-leucine, (S)-N-tetradecoxycarbonylvaline, (S)-N-dodecoxycarbonylphenylglycine, (S)-N-dodecoxycarbonylserine, (S)-N-dodecoxycarbonylalanine, (S)-N-dodecoxycarbonylleucine, and (S)-N-dodecoxycarbonylproline.

15. The kit of claim 12 wherein said cationic surfactant is selected from the group of surfactants consisting of long-chain amines and quaternary ammonium salts.

16. The kit of claim 12 wherein said cationic surfactant is selected from the group consisting of tetradecyltrimethylammonium, cetylpyridinium, dodecyltrimethylammonium, and hexadecyltrimethylammonium.

17. The kit of claim 11 wherein said polyamine has the formula:

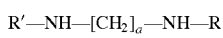

R'—NH—[CH$_2$]$_a$—NH—R wherein a is a numeral from about 1 to 8; and

R and R' are the same or different and may be alkyl, alkenyl or alkynyl substituents, branched or straight chain, substituted or unsubstituted, having from about 1 to 8 carbons, and may have one or more hydrophilic moities such as hydroxy, sulfhydryl, or amine.

18. The kit of claim 11 wherein said polycarboxylate is selected from the group consisting succinnic acid, citric acid, cis-aconitic acid, iso-citric acid, glutaric acid, fumaric acid, malic acid, and oxaloacetic acid.

19. A method for performing electrokinetic chromatography comprising the steps of:
    a) providing a capillary electrophoresis reagent comprising an aqueous phase having a partitioning additive and buffer means for receiving said sample and forming a solution of said analyte;
        (i) said partitioning additive selected from the group consisting of cyclodextrins, polymer ions, proteins and surface active agents, said partitioning additive in an amount to allow partitioning of analyte from solution to the partitioning additive;
        (ii.) buffering means at a concentration to maintain a pH of 2–7 for neutral to acidic aqueous phases and a pH of 7–12 for neutral to basic aqueous phases, said buffering means comprising a polyamine for partitioning additives which are neutral to acidic and a polycarboxylate for partitioning additives which are neutral to basic, said aqueous phase, having a conductivity of 0.5 to 2.0 mS/cm
    b) forming a solution of said analyte in said aqueous phase
    c) injecting said aqueous phase having a solution of analyte into a capillary and imposing a voltage across the capillary to effect a separation of the analyte.

20. The method of claim 19 wherein said partitioning additive is a surface active agent at a concentration to form micelles in said aqueous phase, said surface active agent comprising an anionic surfactant for aqueous phases which are neutral to basic, and said surface active agent comprising a cationic surfactant for aqueous phases which are neutral to acidic.

21. A capillary electrophoresis reagent for isolating one or more analytes contained in a sample, comprising: an aqueous phase for receiving said sample and forming a solution of said analyte, said aqueous phase having a partitioning additive and buffering means, said partitioning additive in an amount to allow partitioning of analyte from solution to the partitioning additive; said buffering means comprising a polyamine for partitioning additives which are neutral to acidic and a polycarboxylate for partitioning additives which are neutral to basic, said buffering means at a concentration to maintain a pH of 2–7 when said aqueous phase is neutral to acidic and a pH of 7–12 when said aqueous phase is neutral to basic, said aqueous phase with said partitioning additive and buffering means having a conductivity of 0.5 to 2.0 mS/cm, wherein said partitioning additive is selected from the group consisting of carboxymethyl-β-cyclodextrin, succinylated-β-cyclodextrin, protonated crown ether acid derivatives, 18-crown-6-tetracarboxylic acid and surface active agents, said surface active agent comprising an anionic surfactant for aqueous phases which are neutral to basic, and said surface active agent comprising a cationic surfactant for aqueous phases which are neutral to acidic, wherein said anionic surfactant is selected from the group of protonated surfactants wherein said cationic surfactant is selected from the group of quaternary ammonium salts with hydroxide counterions consisting of tetradecyltrimethyl ammonium, cetylpyridinium, dodecyltrimethylammonium, and hexadecyltrimethylammonium, wherein said polyamine, has the following structural formula:

wherein a is a numeral from about 1 to 8; and

R and R' are the same or different and may be alkyl, alkenyl or alkynyl substituents, branched or straight chain, substituted or unsubstituted, having from about 1 to 8 carbons, and may have one or more hydrophilic moities such as hydroxy, sulfhydryl, or amine, and wherein said polycarboxylate is selected from the group consisting of succinnic acid, citric acid, cis-aconitic acid, iso-citric acid, glutaric acid, fumaric acid, malic acid, and oxaloacetic acid.

* * * * *